US011529361B2

(12) United States Patent
Sommer et al.

(10) Patent No.: US 11,529,361 B2
(45) Date of Patent: *Dec. 20, 2022

(54) **HALOGENATED SALICYLANILIDES FOR TREATING *CLOSTRIDIUM* INFECTIONS**

(71) Applicant: UNION therapeutics A/S, Hellerup (DK)

(72) Inventors: Morten Otto Alexander Sommer, Virum (DK); Rasmus Vendler Toft-Kehler, København Ø (DK); Daniel Jean Jacques Simon, Soborg (DK)

(73) Assignee: UNION therapeutics A/S, Hellerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/091,691

(22) Filed: Nov. 6, 2020

(65) Prior Publication Data

US 2021/0308153 A1    Oct. 7, 2021

Related U.S. Application Data

(63) Continuation of application No. 16/589,699, filed on Oct. 1, 2019, now Pat. No. 10,857,164, which is a continuation of application No. 15/576,220, filed as application No. PCT/EP2016/061968 on May 27, 2016, now Pat. No. 10,463,680.

(30) Foreign Application Priority Data

May 29, 2015   (GB) .................................. 1509326.3

(51) Int. Cl.
*A61K 31/609* (2006.01)
*A61K 31/612* (2006.01)
*A61P 31/04* (2006.01)
*A61K 45/06* (2006.01)

(52) U.S. Cl.
CPC .......... *A61K 31/609* (2013.01); *A61K 31/612* (2013.01); *A61K 45/06* (2013.01); *A61P 31/04* (2018.01)

(58) Field of Classification Search
None
See application file for complete search history.

(56) References Cited

U.S. PATENT DOCUMENTS

| | | |
|---|---|---|
| 2,731,386 A | 1/1956 | Laszlo |
| 3,674,850 A | 7/1972 | Osborne |
| 3,914,418 A | 10/1975 | Patchett et al. |
| 4,287,191 A | 9/1981 | Coburn et al. |
| 4,310,682 A | 1/1982 | Ozawa et al. |
| 4,358,443 A | 11/1982 | Coburn et al. |
| 4,671,957 A | 6/1987 | Holtshousen |
| 4,742,083 A | 5/1988 | Ritchey |
| 4,883,660 A | 11/1989 | Blackman et al. |
| 4,939,132 A | 7/1990 | Coburn et al. |
| 5,958,911 A | 9/1999 | Evans et al. |
| 6,117,859 A | 9/2000 | Evans et al. |
| 6,251,869 B1 | 6/2001 | Bohanon |
| 6,399,629 B1 | 6/2002 | Chamberland et al. |
| 6,492,425 B1 | 12/2002 | Callahan et al. |
| 6,534,489 B1 | 3/2003 | Jomaa |
| 6,830,758 B2 | 12/2004 | Nichols et al. |
| 8,097,759 B2 | 1/2012 | Muto et al. |
| 8,198,326 B2 | 6/2012 | Scholz |
| 8,263,657 B2 | 9/2012 | Muto et al. |
| 8,618,100 B2 | 12/2013 | Guillemont et al. |
| 8,796,292 B2 | 8/2014 | Wright et al. |
| 8,846,646 B2 | 9/2014 | Chiou |
| 9,446,131 B2 | 9/2016 | Hardas et al. |
| 9,949,988 B2 | 4/2018 | Delavenne et al. |
| 10,463,680 B2 | 11/2019 | Sommer et al. |
| 10,758,553 B2 | 9/2020 | Delavenne et al. |
| 10,857,164 B2 | 12/2020 | Sommer et al. |
| 11,045,434 B1 | 6/2021 | Sommer et al. |
| 11,285,164 B2 | 3/2022 | Delavenne et al. |
| 11,324,708 B1 | 5/2022 | Sommer et al. |
| 11,331,237 B2 | 5/2022 | Smith |
| 2002/0192273 A1 | 12/2002 | Buseman et al. |
| 2003/0036533 A1 | 2/2003 | Jomaa |
| 2003/0045746 A1 | 3/2003 | Jomaa |
| 2004/0071757 A1 | 4/2004 | Rolf |
| 2004/0082549 A1 | 4/2004 | Jomaa |
| 2005/0075511 A1 | 4/2005 | Jomaa |

(Continued)

FOREIGN PATENT DOCUMENTS

| CA | 2344867 | 3/2000 |
|---|---|---|
| CA | 2360661 | 8/2000 |

(Continued)

OTHER PUBLICATIONS

Huang et al (J Am Chem Soc 135:17078-17089, 2013) (Year: 2013).*
Enroth, "Helicobacter pylori ," International Encyclopedia of Public Health, 2nd edition, 3:527-531.
Study ATx201-004, OINTMENT 2% or 4% in Impetigo, 2 pages. (Dec. 1, 2015) UK Standards for Microbiology Investigations, Identification of *Clostridium* species, Bacteriology—Identification, 8(4):27 pages.
Ahn et al. (Mar. 16, 2017) "Anti-helminthic Niclosamide Inhibits Ras-driven Oncogenic Transformation Via Activation of GSK-3," Oncotarget, 8(19):31856-31863.

(Continued)

*Primary Examiner* — Craig D Ricci
(74) *Attorney, Agent, or Firm* — Mintz, Levin, Cohn, Ferris, Glovsky and Popeo, P.C

(57) ABSTRACT

The present invention relates to halogenated salicylanilides, or pharmaceutically acceptable salts or esters thereof, for use in the treatment of an infection in a subject caused by *Clostridium* bacteria, particularly a *C. difficile* infection. The halogenated salicylanilides are expected to be useful in the treatment of *C. difficile* associated diseases including *C. difficile* associated diarrhoea and *C. difficile* associated colitis.

22 Claims, 1 Drawing Sheet

(56) References Cited

U.S. PATENT DOCUMENTS

| | | | |
|---|---|---|---|
| 2006/0052452 | A1 | 3/2006 | Scholz |
| 2006/0122243 | A1 | 6/2006 | Muto et al. |
| 2006/0280783 | A1 | 12/2006 | Dipietro et al. |
| 2007/0059351 | A1 | 3/2007 | Murrell et al. |
| 2010/0029781 | A1 | 2/2010 | Morris |
| 2010/0317643 | A1 | 12/2010 | Goodacre et al. |
| 2013/0005802 | A1 | 1/2013 | Chen et al. |
| 2013/0189368 | A1 | 7/2013 | Mosqueira et al. |
| 2014/0135296 | A1 | 5/2014 | Deretic et al. |
| 2014/0294957 | A1 | 10/2014 | Stein et al. |
| 2015/0104492 | A1 | 4/2015 | Mcdermott et al. |
| 2015/0250808 | A1 | 9/2015 | Deretic et al. |
| 2016/0143987 | A1 | 5/2016 | Engelthaler et al. |
| 2016/0199343 | A1 | 7/2016 | De Visscher et al. |
| 2016/0303034 | A1 | 10/2016 | Collins et al. |
| 2017/0014325 | A1 | 1/2017 | Carola et al. |
| 2017/0056347 | A1 | 3/2017 | Glick et al. |
| 2017/0172943 | A1 | 6/2017 | Hardas et al. |
| 2017/0258816 | A1 | 9/2017 | Delavenne et al. |
| 2017/0304372 | A1 | 10/2017 | Kim et al. |
| 2018/0207179 | A1 | 7/2018 | Sommer et al. |
| 2018/0224470 | A1 | 8/2018 | Leung et al. |
| 2019/0151231 | A1 | 5/2019 | Sommer et al. |
| 2019/0201422 | A1 | 7/2019 | Sommer et al. |
| 2020/0268693 | A1 | 8/2020 | Mylonakis et al. |
| 2020/0306269 | A1 | 10/2020 | Delavenne et al. |
| 2020/0306270 | A1 | 10/2020 | Delavenne et al. |
| 2020/0306271 | A1 | 10/2020 | Delavenne et al. |
| 2021/0137948 | A1 | 5/2021 | Sommer |

FOREIGN PATENT DOCUMENTS

| | | |
|---|---|---|
| CA | 2399947 | 8/2001 |
| CN | 104053632 | 9/2014 |
| CN | 104430338 | 3/2015 |
| DE | 19828097 | 12/1999 |
| DE | 19843334 | 3/2000 |
| DE | 19843360 | 3/2000 |
| DE | 19843383 | 3/2000 |
| DE | 19859426 | 7/2000 |
| EP | 0221211 | 1/1989 |
| EP | 0487973 | 6/1992 |
| EP | 1174439 | 1/2002 |
| EP | 1140952 | 9/2003 |
| EP | 1514544 | 3/2005 |
| EP | 2262754 | 12/2010 |
| EP | 3020398 | 5/2016 |
| FR | 1340175 A | 10/1963 |
| GB | 1421589 A | 1/1976 |
| GB | 1527638 A | 10/1978 |
| GB | 2456376 A | 7/2009 |
| GB | 2465633 A | 6/2010 |
| JP | 2002518307 A | 6/2002 |
| JP | 2004331577 A | 11/2004 |
| JP | 2007007189 A | 1/2007 |
| JP | 2009519709 A | 5/2009 |
| JP | 2009533415 A | 9/2009 |
| JP | 2010528098 A | 8/2010 |
| JP | 2010539179 A | 12/2010 |
| JP | 2011511774 A | 4/2011 |
| JP | 2011526934 A | 10/2011 |
| JP | 2012012338 A | 1/2012 |
| JP | 2012505867 A | 3/2012 |
| JP | 2013529668 A | 7/2013 |
| JP | 2013224320 A | 10/2013 |
| RU | 2227025 C2 | 4/2004 |
| SU | 597671 A1 | 3/1978 |
| WO | 9619220 | 6/1996 |
| WO | 1998056390 | 12/1998 |
| WO | 9965449 | 12/1999 |
| WO | 0004031 | 1/2000 |
| WO | 0016757 | 3/2000 |
| WO | 0017212 | 3/2000 |
| WO | 0044358 | 8/2000 |
| WO | 0044359 | 8/2000 |
| WO | 0048636 | 8/2000 |
| WO | 0160157 | 8/2001 |
| WO | 0160829 | 8/2001 |
| WO | 0193872 | 12/2001 |
| WO | 2002045662 | 6/2002 |
| WO | 03072113 | 9/2003 |
| WO | 2004006906 | 1/2004 |
| WO | 2004047842 | 6/2004 |
| WO | 2004062600 | 7/2004 |
| WO | 2005025598 | 3/2005 |
| WO | 2005074912 | 8/2005 |
| WO | 2006104763 | 10/2006 |
| WO | 2007066130 | 6/2007 |
| WO | 2007119151 | 10/2007 |
| WO | 2008006848 | 1/2008 |
| WO | 2008021088 | 2/2008 |
| WO | 2008039640 | 4/2008 |
| WO | 2008092006 | 7/2008 |
| WO | 2008133982 | 11/2008 |
| WO | 2008155535 | 12/2008 |
| WO | 2009111040 | 9/2009 |
| WO | 2009111064 | 9/2009 |
| WO | 2009140215 | 11/2009 |
| WO | 2010003568 | 1/2010 |
| WO | 2010005836 | 1/2010 |
| WO | 2010043717 | 4/2010 |
| WO | 2010061330 | 6/2010 |
| WO | 2010129062 | 11/2010 |
| WO | 2011098579 | 8/2011 |
| WO | 2012032360 | 3/2012 |
| WO | 2012050826 | 4/2012 |
| WO | 2013182990 | 12/2013 |
| WO | 2014117236 | 8/2014 |
| WO | 2014121342 | 8/2014 |
| WO | 2014125075 | 8/2014 |
| WO | 2014135891 | 9/2014 |
| WO | 2014176634 | 11/2014 |
| WO | 2014200705 | 12/2014 |
| WO | 2015071668 | 5/2015 |
| WO | 2015143654 | 10/2015 |
| WO | 2016004166 | 1/2016 |
| WO | 2016038035 | 3/2016 |
| WO | 2016080846 | 5/2016 |
| WO | 2016138286 | 9/2016 |
| WO | 2016144569 | 9/2016 |
| WO | 2016144979 | 9/2016 |
| WO | 2016193136 | 12/2016 |
| WO | 2016210247 | 12/2016 |
| WO | 2016210289 | 12/2016 |
| WO | 2017040864 | 3/2017 |
| WO | 2017157997 | 9/2017 |
| WO | 2018051102 | 3/2018 |
| WO | 2018141063 | 8/2018 |
| WO | 2018173069 | 9/2018 |
| WO | 2019038443 | 2/2019 |
| WO | 2019053180 | 3/2019 |
| WO | 2019192968 | 10/2019 |
| WO | 2020039073 A1 | 2/2020 |
| WO | 2020091804 A1 | 5/2020 |
| WO | 2020176067 | 9/2020 |
| WO | 2021076922 A1 | 4/2021 |
| WO | 2021198116 A1 | 10/2021 |

OTHER PUBLICATIONS

Akiyama et al. (1999) "Recent Investigations of *Staphylococcus Aureus* in Dermatology," Japanese journal of Dermatology, 109(13):2095-2102.

Amieva et al. (Jan. 1, 2008) "Host-Bacterial Interactions in Helicobacter pylori Infection," Gastroenterology, 134(1):306-323.

Andrews et al. (1983) "The Biology and Toxicology of Molluscicides, Bayluscide," Pharmacology & Therapeutics, 19:245-295.

Babakhani et al. (2012) "Fidaxomicin Inhibits Spore Production in Clostridium Difficile," Infectious Diseases, 55(S2):S162-S169.

Backert et al. (Jul. 15, 2016) "The Role of CagA in the Gastric Biology of Helicobacter pylori," Cancer Research, 76(14):4028-4031.

(56) References Cited

OTHER PUBLICATIONS

Beers et al. (2003) "The Merck Manual of Medical Information, Second Home Edition," 1222-1223.
Bieber (Apr. 3, 2008) "Atopic Dermatitis: Mechanisms of Disease," The New England Journal of Medicine, 358(14):1483-1494.
Burock et al. (2018) "Niclosamide a New Chemotherapy Agent? Pharmacokinetics of the Potential Anticancer Drug in a Patient Cohort of the NIKOLO Trial," Journal of Clinical Oncology, 36(15_suppl):1 page.
Burock et al. (2018) "Phase II Trial to Investigate the Safety and Efficacy of Orally Applied Niclosamide in Patients with Metachronous or Sychronous Metastases of a Colorectal Cancer Progressing after Therapy: The NIKOLO Trial," BMC Cancer, 18(1):7 pages.
Carvalho et al. (2011) "Nitazoxanide Disrupts Membrane Potential and Intrabacterial pH Homeostasis of *Mycobacterium* tuberculosis," ACS Medicinal Chemistry Letters, 2(11):849-854.
Celli et al. (Aug. 25, 2009) "Helicobacter pylori Moves Through Mucus by Reducing Mucin Viscoelasticity," Proceedings of the National Academy of Sciences, 106(34):14321-14326.
Censini et al. (Dec. 1996) "cag, a Pathogenicity Island of Helicobacter pylori, Encodes Type I-specific and Disease-associated Virulence Factors," Proceedings of the National Academy of Sciences, 93(25):14648-14653.
Chan Francis K. (Oct. 4, 2008) "Proton-pump Inhibitors in Peptic Ulcer Disease," The Lancet, 372(9645):1198-1200.
Cheung Dae Y. (Sep. 2017) "Atrophic Gastritis Increases the Risk of Gastric Cancer in Asymptomatic Population in Korea," Gut and Liver, 11(5):575-576.
Chey et al. (Feb. 2017) "ACG Clinical Guideline: Treatment of Helicobacter pylori Infection," American Journal of Gastroenterology, 112(2):212-238.
Chirife et al. (1983) "In Vitro Antibacterial Activity of Concentrated Polyethylene Glycol 400 Solutions," Antimicrobial Agents and Chemotherapy, 24(3):409-412.
Choi et al. (Mar. 22, 2018) "Helicobacter pylori Therapy for the Prevention of Metachronous Gastric Cancer," The New England Journal of Medicine, 378(12):1085-1095.
Chung et al. (Oct. 24-28, 2015) "23rd United European Gastroenterology Week".
Coburn et al. (1981) "Potential Salicylamide Antiplaque Agents: In Vitro Antibacterial Activity against Actinomyces viscosus," Journal of Medicinal Chemistry, 24:1245-1249.
Cooper et al. (Sep. 7, 1998) "Systematic Review of Propionibacterium Acnes Resistance to Systemic Antibiotics," Medical Journal of Australia, 169(5):259-261.
Correa Pelayo (Jun. 2013) "Gastric Cancer: Overview," Gastroenterology Clinics of North America, 42(2):211-217 (8 pages).
Daidone et al. (Jun. 1990) "Salicylanilide and Its Heterocyclic Analogues. A Comparative Study of Their Antimicrobial Activity," Pharmazie, 45(6):441-442.
Damjanov Ivan (May 2005) "Robbins and Cotran Pathologic Basis of Disease, 7th Edition," Shock, 23(5):482-483.
Deen et al. (May 2013) "The Impact of Autophagic Processes on the Intracellular Fate of Helicobacter pylori," Autophagy, 9(5):639-652.
Dobie et al. (2004) "Fusidic Acid Resistance in *Staphylococcus Aureus*," Archives of Disease in Childhood, 89:74-77.
Drago et al. (2005) "In Vitro Selection of Resistance in *Pseudomonas aeruginosa* And *Acinetobacter* Spp. by Levofloxacin and Ciprofloxacin Alone and in Combination with Beta-lactams and Amikacin," The Journal of Antimicrobial Chemotherapy, 56(2):353-359.
Dubois et al. (2007) "Helicobacter pylori is Invasive and it may be a Facultative Intracellular Organism," Cellular Microbiology, 9(5):1108-1116.
Eom et al. (Feb. 22, 2011) "Use of Acid-suppressive Drugs and Risk of Pneumonia: A Systematic Review and Meta-analysis," CMAJ, 183(3):310-319.
Fifer, et al. (Jun. 2016) "Failure of Dual Antimicrobial Therapy in Treatment of Gonorrhea," New England Journal of Medicine 374(25):2504-2506.
Fischer et al. (2006) "Recipe Against Bath Dermatitis," Pharmacy, 3 pages.
Galmiche et al. (Nov./Dec. 2010) "Targeting of Helicobacter pylori VacA to Mitochondria," Gut Microbes, 1(6):392-395.
Ghazi et al. (1986) "Antibacterial Effect and Toxicity of Synthesized Salicylanilide Derivatives," Zentralblatt fur Mikrobiologie, 141(3):225-232.
Giannouli et al. (2014) "Use of Larvae of the Wax Moth Galleria Mellonella as an in Vivo Model to Study the Virulence of Helicobacter Pylori," BMC Microbiology, 14(228):1-10.
Gisbert et al. (2015) "Helicobacter pylori Second-line Rescue Therapy with Levofloxacin-and Bismuth-containing Quadruple Therapy, after Failure of Standard Triple or Non-bismuth Quadruple Treatments," Alimentary Pharmacology & Therapeutics, 41(8):768-775.
Gooyit et al. (Sep. 16, 2016) "Reprofiled Anthelmintics Abate Hypervirulent Stationary-Phase Clostridiumdifficile," Scientific Reports, 6(33642):8 pages.
Graham et al. (2010) "Helicobacter pylori Treatment in the Era of Increasing Antibiotic Resistance," Gut, 59(8):1143-1153.
Graham David Y. (2015) "Helicobacter pylori Update: Gastric Cancer, Reliable Therapy, and Possible Benefits," Gastroenterology, 148(4):719-731.
Zhao et al. (Oct. 2012) "Study on in Vitro Antimicrobial Activity of Closantel to *Staphylococcus Aureus*," Abstract only, Chinese Journal of Nosocomiology, 22(10):01 page.
Guruge et al. (Mar. 31, 1998) "Epithelial Attachment Alters the Outcome of Helicobacter pylori Infection," Proceedings of the National Academy of Sciences, 95(7):3925-3930.
Hagymási et al. (Jun. 7, 2014) "Helicobacter Pylori Infection: New Pathogenetic and Clinical Aspects," World Journal of Gastroenterology, 20(21):6386-6399.
Hamdoun et al. (Mar. 2017) "Drug Repurposing of the Anthelmintic Niclosamide to Treat Multidrug-Resistant Leukemia," Frontiers in Pharmacology, 8(110):1-11.
Hamilton et al. (2018) "Repurposing of Anthelminthics as Anticancer Drugs," Oncomedicine, 3:1-8.
Hassanzadeh et al. (2008) "Bacterial Resistance to Antibiotics in Acne Vulgaris: an in Vitro Study," Indian Journal of Dermatology, 53:122-124.
Hessey et al. (1990) "Bacterial Adhesion and Disease Activity in Helicobacter Associated Chronic Gastritis," Gut, 31:134-138.
Higaki et al. (Sep. 2, 1977) "Susceptibility of Propionibacterium acnes, *Staphylococcus aureus* and *Staphylococcus epidertnidis* to Kampo Formulations," The Journal of International Medical Research, XP055266294, 318-324.
Hlasta et al. (Jul. 21, 1998) "Novel Inhibitors of Bacterial Two-Component Systems with Gram Positive Antibacterial Activity: Pharmacophore Identification Based on the Screening Hit Closantel," Bioorganic & Medicinal Chemistry Letters, 8(14):1923-1928.
Huemer et al. (2018) "Impact of Antibiotic Treatment on Immune-checkpoint Blockade Efficacy in Advanced Non-squamous Non-small Cell Lung Cancer," Oncotarget, 9(23):16512-16520.
Imhann et al. (2016) "Proton Pump Inhibitors Affect the Gut Microbiome," Gut, 65(5):740-748.
Imperi et al. (2013) "New Life for an old drug: Antimicrobial, Agents and Chemotherapy," 557(2):996-1005.
Imramovsky et al. (2009) "Salicylanilide esters of N-protected amino acids as novel antimicrobial agents," Bioorganic and Medicinal Chemistry Letters, 19(2):348-351.
Jakobsson et al. (Mar. 2010,) "Short-Term Antibiotic Treatment Has Differing Long-Term Impacts on the Human Throat and Gut Microbiome," PLoS One, 5(3):1-12.
Kao et al. (Aug. 20, 2018) "The Antiparasitic Drug Niclosamide Inhibits Dengue Virus Infection by Interfering with Endosomal Acidification Independent of mTOR," PLoS One, 12(8):16 pages.
Kato et al. (2002) "Antibiotic Resistance of Helicobacter pylori Strains in Japanese Children," Journal of Clinical Microbiology, 40(2):649-653.
Kita et al. (2001) "CYP2C19 Genotype Related Effect of Omeprazole on Intragastric pH and Antimicrobial Stability," Pharmaceutical Research, 18(5):615-621.

(56) References Cited

OTHER PUBLICATIONS

Kratky et al. (Dec. 2010) "New Amino Acid Esters of Salicylanilides Active Against MDR-TB and Other Microbes," European Journal of Medicinal Chemistry, 45(12):6106-6113.
Kratky et al. (2011) "Salicylanilide Ester Prodrugs as Potential Antimicrobial Agents—a Review," Current Pharmaceutical Design, 17:3494-3505.
Kuipers et al. (Apr. 18, 1996) "Atrophic Gastritis and Helicobacter pylori Infection in Patients with Reflux Esophagitis Treated with Omeprazole or Fundoplication," The New England Journal of Medicine, 334(16):1018-1122.
Kuipers Ernst J. (2006) "Proton Pump Inhibitors and Helicobacter pylori Gastritis: Friends or Foes?," Basic & Clinical Pharmacology & Toxicology, 99(3):187-194.
Lau et al. (Jul. 2001) "Provision of Phenotype-Matched Blood Units: No Need for PreTransfusion Antibody Screening," Haematologica, 86(7):742-748.
Lee et al. (2014) "Helicobacter pylori CagA Promotes Snail-mediated Epithelial-mesenchymal Transition by Reducing GSK-3 Activity," Nature Communications, 5(4423):1-13.
Louie (2011) "Fidaxomicin versus Vancomycin for Clostridium difficile Infection," The New England Journal of Medicine, 364:422-431.
Lundberg et al. (Sep. 2013) "Efficacy of Topical And Systemic Antibiotic Treatment of Meticillin-Resistant *Staphylococcus Aureus* in a Murine Superficial Skin Wound Infection Model," llnternational Journal of Antimicrobial Agents, 42(3):272-275.
Macielag et al. (Jul. 30, 1998) "Substituted Salicylanilides as Inhibitors of Two-component Regulatory Systems in Bacteria," Journal of Medicinal Chemistry, 41(16):2939-2945.
Malfertheiner et al. (2012) "Management of Helicobacter pylori infectiondthe Maastricht IV/ Florence Consensus Report," Gut, 61:646-664.
Matos et al. (2013) "Helicobacter pylori CagA and VacA Genotypes and Gastric Phenotype: A Meta-analysis," European Journal of Gastroenterology & Hepatology, 25(12):1431-1441.
Matyk et al. (2005) "Heterocyclic Isosters of Antimycobacterial Salicylanilides," 60:399-408.
McGuckin et al. (Oct. 2007) "Muc1 Mucin Limits Both Helicobacter pylori Colonization of the Murine Gastric Mucosa and Associated Gastritis," Gastroenterology, 133(4):1210-1218.
Mohammad et al. (2018) "Repurposing Niclosamide for Intestinal Decolonization of Vancomycin-resistant Enterococci," International Journal of Antimicrobial Agents, 51(6):897-904.
Mollaghan et al. (2012) "Antistaphylococcal Activity of Novel Salicylanilide Derivatives," Current Drug Discovery Technologies, 9(1):39-47.
Mook et al. (2017) "Benzimidazole Inhibitors from the Niclosamide Chemotype Inhib Wnt/ß catenin Signaling with Selectivity over Effects on ATP Homeostasis," Bioorganic & Medicinal Chemistry, 25:1804-1816.
Muir et al. (1982) "Degradation of Niclosamide (2',5-dichloro-4'-nitrosalicylanilide) in Sediment and Water Systems," Journal of Agricultural and Food Chemistry, 30(6):1028-1032.
Nemeth et al. (Feb. 2015) "Bacteriostatic Versus Bactericidal Antibiotics for Patients with Serious Bacterial Infections: Systematic Review and Meta-analysis," The Journal of Antimicrobial Chemotherapy, 70(2):382-395.
Nguyen et al. (Sep. 1999) "Host Determinants of Helicobacter Pylori Infection and its Clinical Outcome," Helicobacter pylori, 4(3):185-197.
Nomura et al. (Feb. 2002) "*Staphylococcus aureus* and atopic dermatitis," IRYO, 54(2):62-66.
Noto et al. (2016) "The Mongolian Gerbil: A Robust Model of Helicobacter pylori-Induced Gastric Inflammation and Cancer," Methods in Molecular Biology, 1422:263-280 (20 pages).
Odenbreit Stefan (2005) "Adherence Properties of Helicobacter pylori: Impact on Pathogenesis and Adaptation to the Host," International Journal of Medical Microbiology, 295(5):317-324.
Osmundsen (1969) "Contact Photoallergy to Tribromsalicylanilide," British Journal of Dermatology, 81:429-434.
Ottemann et al. (Apr. 2002) "Helicobacter pylori Uses Motility for Initial Colonization and to Attain Robust Infection," Infection and Immunity, 70(4):1984-1990.
Papastergiou et al. (Jan. 14, 2016) "Helicobacter pylori and Colorectal Neoplasia: Is there a Causal Link?," World Journal of Gastroenterology, 22(2):649-658.
Papastergiou et al. (Aug. 7, 2014) "Treatment of Helicobacter pylori Infection: Meeting the Challenge of Antimicrobial Resistance," World Journal of Gastroenterology, 20(29):9898-9911.
Pauk et al. (2013) "New Derivatives of Salicylamides: Preparation and Antimicrobial Activity Against Various Bacterial Species," Bioorganic & Medicinal Chemistry, 21:6574-6581.
Peek Jr. et al. (Jan. 2002) "Helicobacter pylori and Gastrointestinal Tract Adenocarcinomas," Nature Reviews Cancer, 2(1):28-37.
Pereira et al. (Jan. 21, 2014) "Role of Helicobacter pylori in Gastric Mucosa-associated Lymphoid Tissue Lymphomas," World Journal of Gastroenterology, 20(3):684-698.
Pospisil (Feb. 1971) "lsovitalex—a chemically definable enricher of culture media for Neisseria gonorrhoeae," Ceskoslovenská Dermatol, 46(1):23-25.
Rajamuthiah et al. (2015) "Repurposing Salicylanilide Anthelmintic Drugs to Combat Drug Resistant *Staphylococcus aureus*," PLoS ONE, e0124595, 10(4):19 pages.
Rajamuthiah et al. (Feb. 2014) "Whole Animal Automated Platform for Drug Discovery against Multi-Drug Resistant *Staphylococcus aureus*," PloS One, 9(2):11 pages.
Rodriguez-Cavallini et al. (2004) "Etiologia Bacteriana y Susceptibilidad a Antibioticos en Pacientes con Acne," Rev Biomed, 15:101-106.
Rolfe (1990) "Chemical Resistence in livesteock—an overview," www.regional.org.au/au/roc/1990/roc199029.htm, 18 pages.
Romano et al. (2004) "Eradication of Helicobacter pylori: A Clinical Update," MedGenMed: Medscape general medicine, 6(1):19.
Sanphui et al. (Jul. 24, 2012) "Pharmaceutical Cocrystals of Niclosamide," Crystal Growth & Design, 12(9):4588-4599.
Schenk et al. (2000) "Effect of Helicobacter pylori Eradication on Chronic Gastritis During Omeprazole Therapy," Gut, 46:615-621.
Sekirov et al. (Oct. 2008) "Antibiotic-induced Perturbations of the Intestinal Microbiota Alter Host Susceptibility to Enteric Infection," Infection and Immunity, 76(10):4726-4736.
Shah et al. (May 2003) "High Levels of Fusidic Acid-Resistant *Staphylococcus Aureus* in Dermatology Patients," British Journal of Dermatology, 148(5):1018-1020.
Sherwood et al. (2002) "Impact of Acid Secretion, Gastritis, and Mucus Thickness on Gastric Transfer of Antibiotics in Rats," Gut, 51(4):490-495.
Shimada et al. (Oct. 2007) "Role of Helicobacter Pylori Eradication in the Prevention of Peptic Ulcer in NSAID Users," Nihon Rinsho, 65(10):1824-1829.
Shiota et al. (Sep. 2015) "Antibiotic Resistance of Helicobacter pylori Among Male United States Veterans," Clinical Gastroenterology and Hepatology, 13(9):1616-1624 (17 pages).
Singh et al. (1977) "Synthesis of 5-chloro-3'-nitro-4'-substituted Salicylanilides, a New Series of Antihelmintic and Antimicrobial Agents," Journal of Medicinal Chemistry, 20(6):826-829.
Steffen et al. (Jun. 21, 2011) "Discovery and Structure-Activity Relationships of Modified Salicylanilides as Cell Permeable Inhibitors of Poly(ADP-ribose) Glycohydrolase (PARG)," Journal of Medicinal Chemistry, 54:5403-5413.
Stiefel et al. (Nov. 2006) "Suppression of Gastric Acid Production by Proton Pump Inhibitor Treatment Facilitates Colonization of the Large Intestine by Vancomycin-Resistant *Enterococcus* spp. and Klebsiella pneumoniae in Clindamycin-Treated Mice ," Antimicrob Agents Chemother, 50(11):3905-3907.
SWAN (1999) "The Pharmacology of Halogenated Salicylanilides and Their Anthelmintic Use in Animals," Journal of the South African Veterinary Association, 70(2):61-70.
Taborsky et al. (Sep. 1959) "Substituted Salicylanilides With Antimicrobial Acitvity," Journal of the American Pharmacists Association, XLVIII(9):503-507.

(56) References Cited

OTHER PUBLICATIONS

Takagi et al. (2018) "The Influence of Long-term Use of Proton Pump Inhibitors on the Gut Microbiota: An Age-sex-matched Case-control Study," Journal of Clinical Biochemistry and Nutrition, 62(1):100-105.
Tam et al. (Dec. 7, 2018) "Host-targeted Niclosamide Inhibits C. Difficile Virulence and Prevents Disease in Mice Without Disrupting the Gut Microbiota," Nature Communications, 9(5233):11 pages.
Tharmalingam et al. (Feb. 27, 2018) "Repurposing the Anthelmintic Drug Niclosamide to Combat Helicobacter Pylori," Scientific Reports, Article No. 3701, 8(1):12 pages.
Thompson et al. (Nov. 1, 2017) "P1.07-008 Microbiome & Immunotherapy: Antibiotic Use Is Associated with Inferior Survival for Lung Cancer Patients Receiving PD-1 Inhibitors," Journal of Thoracic Oncology, Abstract Only, 12(11S2):S1998.
Thung et al. (Feb. 2016) "Review Article: the Global Emergence of Helicobacter Pylori Antibiotic Resistance," Alimentary Pharmacology & Therapeutics, 43(4):514-533.
Uemura et al. (Aug. 1997) "Effect of Helicobacter Pylori Eradication on Subsequent Development of Cancer After Endoscopic Resection of Early Gastric Cancer," Cancer Epidemiol Biomarkers Prev, 6(8):639-642.
Unemo Magnus (2015) "Current and Future Antimicrobial Treatment of Gonorrhoea—The Rapidly Evolving Neisseria Gonorrhoeae Continues to Challenge," BMC Infectious Diseases, 15(364):15 pages.
Van Tonder et al. (2004) "Preparation and Physicochemical Properties of Niclosamide Anhydrate and two Monohydrates," International Journal of Pharmaceutics, 269(2):417-432.
Vinsova et al. (2007) "Salicylanilide Acetates: Synthesis and Antibacterial Evaluation," Molecules, 12(1):1-12.
Vinsova et al. (2014) "Salicylanilide Diethyl Phosphates: Synthesis, Antimicrobial Activity and Cytotoxicity," Bioorganic & Medicinal Chemistry, 22:728-737.
Vinsova et al. (2004) "Salicylanilides: Still a Potential Antibacterially Active Group," Ceska Slov Farm, 53(6):294-299.
Waisser et al. (2003) "Antimycobacterial and Antifungal Isosterd of Salicylanilides," Arch Pharm (Weinheim), 336:322-335.
Waisser et al. (2001) "Synthesis and Antimycobacterial Activity of Salicylanilides Substituted in Position 5," Chemical Papers, 55(2)121-129.
Waisser et al. (2006) "The Oriented Development of Antituberculotics: Salicylanilides," Arch Pharm (Weinheim), 339:616-620.
Wu et al. (2014) "Antihelminthic Niclosamide Modulates Dendritic Cells Activation and Function," Cellular Immunology, 288:15-23.
Wu et al. (Jan. 2013) "Diagnostic Accuracy of Narrow-band Imaging for the Differentiation of Neoplastic from Non-neoplastic Colorectal Polyps: a Meta-analysis," Colorectal Disease, 15(1):3-11.
Wulff et al. (Jun. 2007) "Cream Formulations Protecting Against Cercarial Dermatitis by Trichobilharzia," Parasitology Research, 101(1):91-97.
Yamaoka et al. (1997) "Induction of Various Cytokines and Development of Severe Mucosal Inflammation by cagA Gene Positive Helicobacter Pylori Strains," Gut, 41(4):442-451.
Yu et al. (2018) "Niclosamide Exhibits Potent Anticancer Activity and Synergizes with Sorafenib in Human Renal Cell Cancer Cells," Cellular Physiology and Biochemistry, 47(3):957-971.

Yutin et al. (Oct. 2013) "A Genomic Update on Clostridial Phylogeny: Gram-negativespore-formers and Other Misplaced Clostridia,," Environ Microbial, 15(10): 2631-2641.
Zhao et al. (Mar. 2012) "Antimicrobial Activity Testing for Closantel to the *Staphylococcus aureus* in Vitro," Department of Clinical Microbiology,Zhejiang Provinical People's Hospital; Zhejiang Journal of Medicine, 22(10):2019-2021 (5 pages).
U.S. Appl. No. 17/290,386, filed Apr. 30, 2021, 156 pages.
Devine et al. (Feb. 1970) "Spectra of Susceptibility of Neisseria meningitidis to Antimicrobial Agents In Vitro", Journal of Applied Microbiology, 19(2):329-334.
Gu Hy. (2008) "The Study on the Mechanisms of Helicobacter pylori Motility in Gastric Mucosal Colonization", Chinese Journal of Laboratory Medicine, 31:733-736.
Hassan et al. (Dec. 1991) "Topical Niclosamide as a Protective Agent Against Schistosome Infection", Journal of the Egyptian Society of Parasitology, 21(3):817-822.
Jabs, et al. (2000) "Guidelines for the Use of Immunosuppressive Drugs in Patients with Ocular Inflammatory Disorders: Recommendations of an Expert Panel" American Journal of Ophthalmology, 130(4):492-513.
Ofori-Adjei et al. (2008) "A Review of the Safety of Niclosamide, Pyrantel, Triclabendazole and Oxamniquine" The International Journal of Risk & Safety in Medicine, 20:113-122.
Pearson et al. (1985) "Niclosamide Therapy for Tapeworm Infections" Annals of Internal Medicine, 102(4):550-551.
Cheng et al. (2010) "High-throughput Identification of Antibacterials Against Methicillin-resistant *Staphylococcus aureus* (MRSA) and the Transglycosylase", Bioorganic & Medicinal Chemistry, 18(24):8512-8529.
Garza-González et al. (Feb. 14, 2014) "A Review of Helicobacter Pylori Diagnosis, Treatment, and Methods to Detect Eradication", World Journal of Gastroenterology, 20(6): 1438-1449.
Gwisai et al. (2017) "Repurposing Niclosamide as a Versatile Antimicrobial Surface Coating Against De vice-Associated, Hospital-Acquired Bacterial Infections", Biomedical Materials, 12(4):045010(25 pages).
Hu et al. (May 5, 2017) "Novel and Effective Therapeutic Regimens for Helicobacter pylori in an Era of Increasing Antibiotic Resistance", Frontiers in Cellular and Infection Microbiology, 7:168(20 pages).
Kadri et al. (2018) "Niclosamide, a Drug with Many (Re)purposes", ChemMedChem, 13(11):1088-1091.
Krátký et al. (2016) "Salicylanilide N-monosubstituted Carbamates: Synthesis and In Vitro Antimicrobial Activity", Bioorganic & Medicinal Chemistry, 24(6):1322-1330.
Sun et al. (1999) "Antituberculosis Activity of Certain Antifungal and Antihelmintic Drugs", Tubercle and Lung Disease: The Official Journal of the International Union against Tubercolosis and Lung Disease, 79(5):319-320.
Van Doorn et al. (2000) "Importance of Helicobacter Pylori cagA and vacA status for the Efficacy of Antibiotic Treatment", Gut, 46:321-326.
Zhu et al. (2009)" Quantitative High-throughput Screening Identifies Inhibitors of Anthrax-induced Cell Death", Bioorganic & Medicinal Chemistry, 17(14):5139-5145.

\* cited by examiner

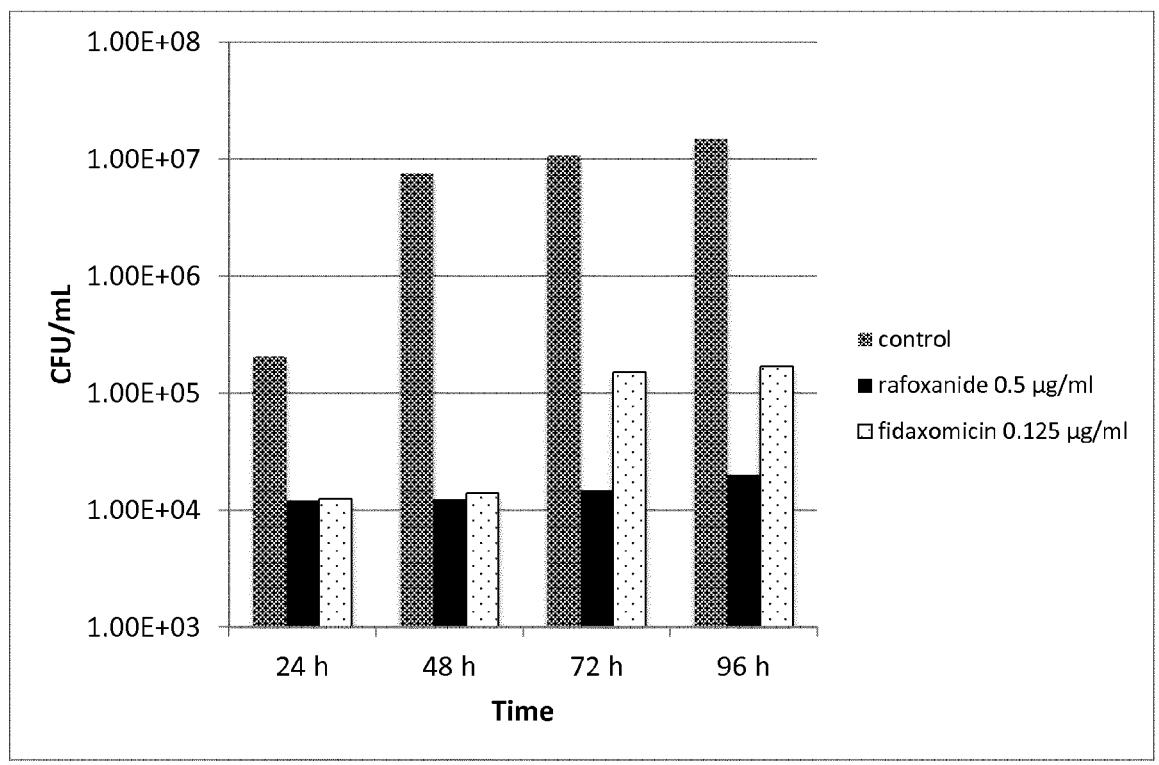

HALOGENATED SALICYLANILIDES FOR TREATING *CLOSTRIDIUM* INFECTIONS

This application is a continuation of and claims priority to U.S. patent application Ser. No. 16/589,699, filed Oct. 1, 2019, which is a continuation of and claims priority to U.S. patent application Ser. No. 15/576,220, filed Nov. 21, 2017, which is the national stage entry of PCT Application No. PCT/EP2016/061968, filed May 27, 2016, which claims priority to Great Britain Patent Application No. 1509326.3, filed May 29, 2015. The entire contents of these applications are incorporated herein by reference in their entirety for all purposes.

This invention relates to halogenated salicylanilides for use in the prevention or treatment of infections caused by *Clostridium* bacteria, particularly *Clostridium difficile*.

BACKGROUND OF THE INVENTION

*Clostridium* is a genus of spore forming Gram-positive bacteria that grow under anaerobic conditions comprising more than 100 species. There are four main species responsible for diseases in humans and other warm-blooded animals: *C. botulinum*, an organism producing a toxin in food or wounds that causes botulism; *C. difficile*, which can cause pseudomembraneous colitis, toxic megacolon and antibiotic associated diarrheas; *C. tetani*, which is the causative organism of tetanus; and *C. perfringens*, which can cause enterotoxemia, necrotizing enteritis, and gas gangrene.

*C. perfringens* is ubiquitous in the environment and is found in soil, dust, raw ingredients such as spices used in food processing, and in the intestines of humans and animals. It produces over 15 different toxins resulting in various enteric conditions. *C. perfringens* infections can also cause gut health problems in broiler flocks with significant negative economic consequences.

*C. difficile* is an opportunistic gram positive, anaerobic, spore forming *bacillus*, and causes *Clostridium difficile* infections (CDI) such as antibiotic-associated diarrhoea (CDAD) and colitis which burdens healthcare systems across the globe. In the last decade, rates of *C. difficile* infections have increased dramatically, particularly hospital-acquired infection (nosocomial infection), resulting in increased morbidity, an increased incidence of complications requiring colectomy, and rising mortality.

It is estimated that 3 to 15% of the normal population is infected with *C. difficile*. However, rates of infection are much higher in hospitalised patients. *C. difficile* colonises the intestine and in many subjects infected the bacteria lives in equilibrium with other gut flora and is asymptomatic. However, if the homoeostasis of the normal intestinal flora is disturbed, for example as a result of previous antibiotic use, the use of drugs which alter the gastric pH (for example proton pump inhibitors), or gastrointestinal surgery, symptomatic CDI can arise as a result of the proliferation of the *C. difficile* in the intestine. Toxins produced by the *C. difficile* disrupt the colonic epithelium, leading to an inflammatory response and clinical symptoms varying from mild diarrhoea to severe life-threatening pseudomembranous colitis.

*C. difficile* bacteria produce toxins, which can cause inflammation and damage to the lining of the lower gastrointestinal tract, including the colon. There are a number of different strains of *C. difficile*, some of which can cause more serious illnesses than others. Strain NAP1/027/BI 027 (NAP1/027) produces particularly high levels of toxins and is associated with particularly severe CDI and high levels of mortality.

*C. difficile* infections are particularly associated with the clinical use of broad spectrum antibiotics, for example clindamycin, cephalosporins and amoxicillin-clavulinic acid). Fluoroquinolone antibiotics have been identified as a particular risk factor for CDI. Antibiotics commonly used to treat a primary infection in a subject (for example a urinary infection, a skin infection or other infection), kill the bacteria that cause the primary infection. However, they may also kill many of the bacteria present in the flora of the GI tract. Because *C. difficile* bacteria are not affected by many commonly used antibiotics this can result in the proliferation of *C. difficile* in the intestine and the presence of high levels of associated toxins resulting in the emergence of symptoms of a CDI.

*C. difficile* infection is the most common infectious cause of nosocomial diarrhoea in elderly patients, accounting for 15% to 25% of all cases of antibiotic-induced diarrhoea. Patients undergoing total joint arthroplasty are at particular risk of CDI because of the advanced age of the patients, the use of prophylactic antibiotic coverage in the perioperative period, multiple comorbid conditions, and length of hospital stay required for recovery.

The treatment of *C. difficile* infections depends on the severity of the associated symptoms or disease. Generally asymptomatic infections are not treated. However, if symptoms develop treatments are generally required to reduce the symptoms and prevent the infection from worsening.

Generally a first step in the treatment of CDI is the cessation of the inciting antibiotic. Treatment with concomitant antibiotics (i.e. antibiotics other than those given to treat *C. difficile* infection) is associated both with significant prolongation of diarrhoea and with an increased risk of recurrent CDI. If concomitant antibiotics are essential for treatment of the primary infection, it is generally prudent, if possible, to use an antibiotic therapy that is less frequently implicated in antibiotic-associated CDI, such as parenteral aminoglycosides, sulfonamides, macrolides, vancomycin, or tetracycline (Lakartidningen, 103(46), 2006).

*C. difficile* infection, such as CDAD is usually treated with metronidazole or oral vancomycin. A new antibiotic against *C. difficile* has recently been approved, fidaxomicin (OPT-80, PAR-101), a macrocyclic antibiotic. In phase III clinical trials, fidaxomicin was non-inferior to vancomycin in achieving clinical cure of CDAD. Fidaxomicin treatment was also superior to vancomycin in preventing recurrence of CDAD. These results, combined with the ease of administration and a somewhat better safety profile has made fidaxomicin an attractive treatment option for treating CDAD. (Louie, T. J., Miller, M. A., Mulvane, K. M., Weiss, K., Lenten, A. Shoe, Y. K. (2011). Fidaxomicin versus Vancomycin for *Clostridium difficile* infection. New England Journal of Medicine, 364, 422-431). However, resistance towards metronidazole, vancomycin and fidaxomicin has been observed.

Rifamycins and derivatives, for example rifampicin and rifaximin, have been successfully used to treat recurrent CDI. However, rapid spontaneous resistance evolution has also been observed with this class of antibiotic and the spread of, for example rifampicin-resistant *C. difficile* in hospitals is an increasing concern.

Teicoplanin (although not widely available and expensive) is another antibiotic with high reported efficacy against CDI, and limited data suggest that it may be effective in recurrent CDI.

Patients who have had one CDI are at risk of recurrence of the infection. The rate of recurrent CDI (RCDI) is estimated to be 15% to 30%. Patients with recurrent *C.*

*difficile* infections in hospitals and the community constitute an increasing treatment problem. Whilst most patients with a first infection respond to either metronidazole or oral vancomycin, current therapeutic approaches to recurrent *C. difficile* infections are prone to failure, increasing the risk of antibiotic resistance emerging. Most treatment guidelines recommend prolonged oral vancomycin pulse and/or tapering dosage regimens. However, evidence supporting the effectiveness of such dosage regimens is limited.

The spores formed by *C. difficile* are thought to be the primary mechanism for the transmission or spread of infection. Additionally spores present in the colon of a patient may be responsible for recurrence of *C. difficile* infections, even after elimination of the bacterial with antibiotic treatment. Fidaxomycin has been shown to inhibit *C. difficile* spore formation (Babakhani et al, S162 CID 2012:55 (suppl 2)). There is however a need for additional agents that can inhibit spore formation and thus minimise the risk of transmission and/or recurrence of *C. difficile* infections.

US patent, U.S. Pat. No. 8,618,100 discloses chromanyl derivatives described as having antibacterial activity against *Clostridium* bacteria, in particular *Clostridium perfringens*.

PCT patent application WO2008/039640 discloses the compound 5-[3-((R)(+)-6,8-dibromo-chroman-4-ylamino)-propylamino]-4H-thieno[3,2-b]pyridine-7-one, which is also known as REP3123, and its antibacterial activity against *Clostridium difficile*. In vitro tests of the antibacterial activity of the REP3123 compound demonstrate that said compound is active against bacteria of the *Clostridium* genus however REP3123 also has antibacterial activity against a wide variety of bacteria that are present in the gut.

U.S. Pat. No. 8,796,292 discloses that certain 7-substituted-2-(benzylamino)-6-oxopurines have potent activity against the growth of the intestinal anaerobe *C. difficile*, but weak activity against other, intestinal Gram-positive anaerobes. The compounds are described to be useful in reducing the likelihood of developing or to treat *C. difficile* infections.

PCT application WO2014135891 describes the rectal administration of compositions comprising fidaxomicin. The compositions are described as useful for the treatment or maintenance of remission of infections such as diarrhea caused by *C. difficile*.

PCT application WO2012/050826 describes the use of reutericyclin or reutericyclin analogs in order to kill *C. difficile* organisms and thus alleviate the signs and symptoms of *C. difficile* infection.

There is however a need for new treatments for *C. difficile*.

Halogenated salicylanilides such as niclosamide, closantel and rafoxanide, are important anthelmintics that are used extensively in the control of *Haemonchus* spp. and *Fasciola* spp. infestation in sheep and cattle, and *Oestrus ovis* in sheep.

Niclosamide is commercially available in a number of formulations including, but not limited to Bayer73®, Bayer2353®, Bayer25648®, Bayluscid®, Baylucide®, Cestocid®, Clonitralid, Dichlosale®, Fenasal®, HL 2447®, Lomesan®, Lomezan®, Manosil®, Nasemo®, Niclosamid®, Phenasal®, Tredemine®, Sulqui®, Vermitid®, Vermitin® and Yomesan®.

Niclosamide has been proposed as a possible systemic treatment for chronic lung infections caused by the proteobacterium *Pseudomonas aeruginosa* and the actinobacterium *Mycoplasmum tuberculosis* (F. Imperi et al., Antimicrobial, Agents and Chemotherapy, 557(2), 996-1005 (2013)).

J. Vinsova et al. (*Molecules*, vol. 12, no. 1, pp. 1-12, 2007; *Bioorganic and Medicinal Chemistry Letters*, vol. 19, no. 2, pp. 348-351, 2009; *European Journal of Medicinal Chemistry*, vol. 45, no. 12, pp. 6106-6113, 2010) describe certain antibacterial activity of salicylanilides, however, there is no disclosure of the treatment of Ca Ghazi et al. (Zentralbl. Mikrobiol. 141 (1986), 225-232) have tested the antibacterial effect and toxicity of synthesized salicylanilide derivatives against *Escherichia coli*, *Bacillus subtilis*, *Pseudomonas aeruginosa* and *Staphylococcus aureus*.

M. J. Macielag et al. tested for antibacterial activity of closantel and related derivatives against the drug-resistant organisms, methicillin-resistant *Staphylococcus aureus* (MRSA) and vancomycin-resistant *Enterococcus faecium* (VREF) (J. Med. Chem., 41(16), 2939-45 (1998)).

D. J. Hlasta et al. found that closantel had antibacterial activity against drug resistant *S. aureus* and *E. faecium* (Bioorg. Med. Chem. Letters, 8(14), 1923-28 (1998)).

R. Rajamuthiah et al. (PloS One, 2014, 9(2): e89189) identified closantel as a hit in a high throughput liquid screening assay and found anti-staphylococcal activity of closantel against vancomycin-resistant *S. aureus* isolates and other Gram-positive bacteria.

R. Rajamuthiah et al. (PloS One, 2015, 10(4):e0124595) describe that niclosamide and oxyclosanide have activity against MRSA.

Pauk et al. Bioorg. & Med. Chem. 23, 6574-6581 (2013), discloses the in-vitro antimicrobial activity of certain halogenated salicylanilides and derivatives.

WO 2008/155535 describes the use of halogenated salicylanilides for the treatment of acne resulting from propioni bacterial infection.

BRIEF SUMMARY OF THE DISCLOSURE

It has been found that halogenated salicylanilides (for example tetrachlorosalicylanilide, closantel, rafoxanide, oxyclozanide, resorantel, clioxanide, dibromosalan, tribromosalan and niclosamide) are active against *Clostridium* bacteria, particularly *C. difficile* and may be useful in treating and/or preventing or reducing *Clostridium* infection and possible reoccurrence of the infection. Use of halogenated salicylanilides may also reduce the rate of developing antibiotic resistance compared to known antibiotics used for the treatment of *Clostridium* infections.

In accordance with the present invention, there is provided a halogenated salicylanilide, or a pharmaceutically acceptable salt or ester thereof, for use in the treatment of an infection in a subject caused by *Clostridium* bacteria.

The infection may be caused by a *Clostridium* bacteria selected from for example, *C. perfringens*, *C. difficile*, *C. botulinum*, *C. tetani*, *C. absonum*, *C. argentinense*, *C. baratii*, *C. bifermentans*, *C. beijerinckii*, *C. butyricum*, *C. cadaveris*, *C. camis*, *C. celatum*, *C. clostridioforme*, *C. cochlearium*, *C. cocleatum*, *C. fallax*, *C. ghonii*, *C. glycolicum*, *C. haemolyticum*, *C. hastiforme*, *C. histolyticum*, *C. indolis*, *C. innocuum*, *C. irregulare*, *C. leptum*, *C. limosum*, *C. malenominaturn*, *C. novyi*, *C. oroticum*, *C. oedematiens*, *C. paraputrificum*, *C. piliforme*, *C. putrefasciens*, *C. ramosum*, *C. septicum*, *C. sordelii*, *C. sphenoides*, *C. spiroforme*, *C. sporogenes*, *C. subterminale*, *C. symbiosum*, *C. tertium* or *C. tetani*.

In one embodiment the bacteria causing the infection is not *C. perfringens*.

The infection is particularly an infection caused by *C. difficile*.

Infection by *Clostridium difficile* may result in a *C. difficile* disease in the subject. The *C. difficile* disease may be, for example, diarrhoea, colitis (including pseudomembranous colitis) or toxic megacolon. The *C. difficile* infection may be *C. difficile* associated diarrhoea. The *C. difficile* infection may be *C. difficile* associated colitis, for example pseudomembranous colitis. The *C. difficile* infection may be *C. difficile* associated bloating. The *C. difficile* infection may be *C. difficile* associated abdominal pain.

*C. difficile* infection in a subject generally arises as a result of the treatment of an infection with an antibiotic. The use of antibiotics to treat an infection will kill the organism causing the underlying infection. However, the antibiotic may also kill many of the bacteria present in the GI tract. The disruption of the normal gut flora can result in the proliferation of the *C. difficile* and emergence of effects of the infection including diarrhoea and colitis. Accordingly it may be that the halogenated salicylanilide is for use in the treatment of an antibiotic induced *Clostridium* infection, particularly an antibiotic induced *C. difficile* infection.

It may be that the antibiotic responsible for the antibiotic induced *Clostridium* infection is an antibiotic other than a halogenated salicylanilide. It may be that the antibiotic responsible for inducing the *Clostridium* infection is an antibiotic used to treat a primary infection in the body other than a *Clostridium* infection (e.g. other than a *C. difficile* infection). For example, the primary infection may be a skin infection, a urinary tract infection, a lung infection or a bone infection. The antibiotic responsible for inducing the infection may be a broad spectrum antibiotic which may be active against Gram positive and/or Gram negative organisms. The antibiotic may be selected from clindamycin, a cephalosporin (for example cefotaxime and ceftaidime), ampicillin, amoxicillin and a quinolone (for example a fluoroquinolone, optionally ciprofloxaxin or levofloxacin). For example, the antibiotic induced *C. difficile* infection may be caused by a fluoroquinoline antibiotic, including but not limited to ciprofloxaxin or levofloxacin.

Although *C. difficile* infections are generally caused by prior use of antibiotics to treat an underlying infection, *C. difficile* infections may also be arise without the prior use of an antibiotic. For example, a reduction in the acidity of the stomach can result in colonization of the normally sterile upper gastrointestinal tract. The use of gastric acid suppressive agents, such as proton pump inhibitors (PPIs) and histamine H2-receptor antagonists (H2RAs) may therefore be associated with an increased risk of *C. difficile* colonization and subsequent development of CDAD. PPIs include, but are not limited to, omeprazole (Losec, Prilosec, Zegerid), lansoprazole (Prevacid, Zoton, Inhibitol), esomeprazole (Nexium), pantoprazole (Protonix, Somac, Pantoloc, Pantozol, Zurcal, Pan) and rabeprazole (Rabecid, Aciphex, Pariet, Rabeloc). H2RAs include, but are not limited to, cimetidine (Tagamet), ranitidine (Zinetac, Zantac), famotidine, (Pepcidine, Pepcid), roxatidine (Roxit) and nizatidine (Tazac, Axid). It may be that the halogenated salicylanilide is for use in the treatment of a *Clostridium* infection (for example a *C. difficile* infection) induced by a gastric acid suppressive agent. Accordingly it may be that the halogenated salicylanilide is for use in treating a *Clostridium* infection in a subject that is or has been treated with a gastric acid suppressive agent, for example a PPI. Accordingly the halogenated salicylanilide may be for use in treating a *Clostridium* infection in a subject treated with a H2RA.

*C. difficile* infection associated disease may also arise spontaneously, particularly when the subject is infected with certain stains of *C. difficile*, for example an infection caused by the NAP1/027/B strain which produces high levels of Toxin A, Toxin B and other toxins.

The halogenated salicylanilide may be used as the first line treatment of a *Clostridium* infection, for example a *C. difficile* infection. By "first-line" treatment is meant the first treatment of the *Clostridium* infection. In the first line treatment the *Clostridium* infection has not been treated with an antibiotic active against the *Clostridium* infection, for example, metronidazole, vancomycin, fidaxomicin or a rifamycin such as rifaximin. Accordingly, it may be that the halogenated salicylanilide is for use in the treatment of a *Clostridium* infection (for example *C. difficile* infection), wherein the infection has not been treated with an antibiotic prior to administration of the halogenated salicylanilide to the subject.

The halogenated salicylanilide may be used to treat a recurrent *Clostridium* infection (e.g. a *C. difficile* infection), for example a *Clostridium* infection which has recurred following prior treatment of the subject with an antibiotic (or other agent) other than a halogenated salicylanilide. For example, the halogenated salicylanilide may be used to treat a *Clostridium* infection (for example a *C. difficile* infection) which has recurred in a subject following prior treatment of the subject with an antibiotic selected from metronidazole, vancomycin, fidaxomicin and a rifamycin such as rifaximin. Suitably an antibiotic selected from metronidazole, vancomycin and fidaxomicin.

The halogenated salicylanilide may be used to treat a *Clostridium* infection (for example a *C. difficile* infection) which is refractory (for example non-responsive) to treatment with an antibiotic (or other agent) other than a halogenated salicylanilide. For example, the halogenated salicylanilide may be used to treat a refractory *Clostridium* infection (for example a *C. difficile* infection) in a subject. Accordingly, the halogenated salicylanilide may be for use in the treatment of a *Clostridium* infection (e.g. *C. difficile*) that is refractory to a prior antibiotic treatment other than a halogenated salicylanilide. For example the halogenated salicylanilide may be used to treat a *C. difficile* in a subject, wherein the *C. difficile* is refractory to treatment of the subject with an antibiotic selected from metronidazole, vancomycin, fidaxomicin and a rifamycin such as rifaximin.

It may be that the halogenated salicylanilide is used to treat a *Clostridium* infection (for example a *C. difficile* infection) which is resistant to an antibiotic agent used to treat the *Clostridium* infection. Accordingly there is provided a halogenated salicylanilide, or a pharmaceutically acceptable salt thereof, for use in the treatment of a *Clostridium* infection (for example a *C. difficile* infection) which is resistant to an antibiotic agent other than the halogenated salicylanilide.

It may be that the *Clostridium* (for example a *C. difficile*) is resistant to an antibiotic agent approved by the US FDA or European Medicines Agency prior to 27 May 2016, preferably an antibiotic approved for use in the treatment of a *Clostridium* infection (for example a *C. difficile* infection). It may be that the *Clostridium* (for example a *C. difficile*) which is resistant to an antibiotic other than the halogenated salicylanilide. It may be that the *Clostridium* (for example a *C. difficile*) which is resistant to an antibiotic selected from a penicillin, a cephalosporin, a carbapenem, a monobactam (for example a β-lactam antibiotic), a fusidane, a fluoroquinolone, a tetracycline, a glycylcycline, phenicol (for example chloramphenicol), a macrolide, a macrocyclic (for example fidaxomicin), a rifamycin, a ketolide, a lincosamide, an oxazolidinone (for example cadazolid), an aminocyclitol, a polymyxin, a glycopeptide, an aminoglycoside, a lipopeptide, an antimycobacterial, a nitroimidazole, bacitracin, mupiricin, a pleuromutilin, a rifamycin, a sulphonamide and trimethoprim.

It may be that the *Clostridium* (for example a *C. difficile*) is resistant to an antibiotic selected from a nitroimidazole, for example metronidazole; a benzimidazole, for example ridinilazole (SMT19969); a glycopeptide, for example vancomycin; a macrocyclic antibiotic, for example fidaxomicin; an oxazolidinone, for example cadazolid; a lipopeptide, for example surothromycin or daptomycin; a glycylcycline, for example tigecycline; a DNA Minor Groove Binder (for example MGB-BP-3) a glycolipodepsipeptide (for example ramoplanin); CRS3123 (a Methionyl-tRNA synthetase (MetRS) inhibitor, Crestone Inc); and a rifamycin such as rifaximin. For example it may be that the *Clostridium* (for example a *C. difficile*) is resistant to an antibiotic selected from metronidazole, vancomycin, fidaxomicin and a rifamycin (e.g. rifaximin).

The *C. difficile* infection may be any strain of *C. difficile* for example the *C. difficile* strains shown in Table 1 below, in which the NCTC number is the UK National Collection of Type Culture reference number.

TABLE 1

| NCTC no. | Ribotype and Toxin Status |
| --- | --- |
| NCTC 11209 (T) | Type strain, PCR-ribotype 001 reference strain |
| NCTC 11204 | PCR-ribotype 001, toxin A and B positive |
| NCTC 11205 | PCR-ribotype 001, toxin A and B positive |
| NCTC 11207 | PCR-ribotype 001, toxin A and B positive |
| NCTC 11208 | PCR-ribotype 001, toxin A and B positive |
| NCTC 11223 | PCR-ribotype 001, toxin A and B positive |
| NCTC 11382 | PCR-ribotype 001, toxin A and B positive |
| NCTC 12729 | PCR-ribotype 002, toxin A and B positive |
| NCTC 13287 | PCR-ribotype 017, toxin A negative, toxin B positive |
| NCTC 13307 | PCR-ribotype 012, toxin A and B positive |
| NCTC 13404 | PCR-ribotype 106 reference strain, toxin A and B positive |
| NCTC 13366 | PCR-ribotype 027 reference strain, toxin A and B positive |

T = Type Strain

It may be that the *C. difficile* infection is a strain of *C. difficile* which produces high levels of Toxin A (entero toxin) and/or Toxin B (cytotoxin). For example it may be that the *C. difficile* infection is a strain of *C. difficile* which produces higher levels of Toxin A than NCTC 11209 (T). It may be that the the *C. difficile* infection is a strain of *C. difficile* which produces higher levels of Toxin B than NCTC 11209 (T). It may be that the the *C. difficile* infection is a strain of *C. difficile* which produces higher levels of Toxin A and Toxin B than NCTC 11209 (T).

The *C. difficile* infection may be the hyper-virulent BI/NAP1 (also known as ribotype 027, NAP1/027/BI or NCTC 13366) strain which shows increased Toxin A (entero toxin) and Toxin B (cytotoxin) production as well as the production of additional novel binary toxins. Accordingly, the halogenated salicylanilide may be for use in the treatment of a *C. difficile* caused by the NAP1/027/BI *C. difficile* strain.

*C. difficile* is an anaerobe and as such the bacteria itself is generally not the primary mechanism for the transmission of infection, because the bacterial is not viable in aerobic conditions. However, *C. difficile* produces spores which are metabolically dormant and very stable. Spores shed in faecal matter are therefore very difficult to eradicate and may persist in the environment for prolonged periods of time, because they are resistant to heat and common cleaning and sterilisation chemicals. The spores represent the primary mechanism for the transmission of *C. difficile* infections. Current treatments for *C. difficile*, for example, metronidazole, vancomycin and rifamycins are effective against *C. difficile*. However, these compounds have limited effects on sporulation and may not effective in preventing transmission of infections by the spores. Fidaxomicin has been shown to be superior to metronidazole, vancomycin, and rifaximin in inhibiting sporulation and as such is currently considered to be the "gold-standard" treatment of *C. difficile* infections because of its potential to also inhibit transmission of infection.

As illustrated in the Examples below, halogenated salicylanilides (for example rafoxanide) are effective inhibitors of *C. difficile* sporulation. In the study performed in the Examples, rafoxanide was more effective than fidaxomicin in inhibiting sporulation. Accordingly it is expected that the halogenated salicylanilides will provide an effective treatment which both kills the *C. difficile* bacteria and inhibits *C. difficile* sporulation. The halogenated salicylanilides are therefore expected to provide an effective treatment of the initial *C. difficile* infection and also prevent or minimise the risk of transmission or spread of infection, for example spread of infection in a community or hospital environment.

Accordingly there is provided a halogenated salicylanilide, or a pharmaceutically acceptable salt or ester thereof (for example rafoxanide), for use in preventing or inhibiting sporulation of *C. difficile*.

Also provided is a halogenated salicylanilide, or a pharmaceutically acceptable salt or ester thereof (for example rafoxanide), for use in preventing or inhibiting transmission or spread of a *C. difficile* infection.

Also provided is a halogenated salicylanilide, or a pharmaceutically acceptable salt or ester thereof (for example rafoxanide), for use in a method of preventing or inhibiting transmission or spread of a *C. difficile* infection, the method comprising administering the halogenated salicylanilide, or a pharmaceutically acceptable salt or ester thereof to a subject with a *C. difficile* infection.

A common problem associated with *C. difficile* infection is the recurrence of the infection following initial antibiotic treatment. Often a patient will respond well to the initial antibiotic treatment and will be symptom free for a period of time. However, in many patients recurrence of the infection is common and is often more severe than the initial infection (Louie T J, et al. N. Eng. J. Med 2011; 364: 422-31). Mortality rates increase as the frequency of recurrent infection increases. A primary factor in the recurrence of infection is thought to be spores residing in the GI tract, particularly in the colon of a patient who has previously had a *C. difficile* infection. Spores present in the colon of a patient that has been infected with *C. difficile* and can persist there in a dormant state for long periods of time. Upon activation the spores result in recurrence of the infection. The sporulation inhibitory properties of the halogenated salicylanilides are therefore expected to be beneficial in the prevention or reduction of the recurrence of *C. difficile* infection by reducing or eliminating spore formation in a patient infected with *C. difficile*.

Accordingly also provided is a halogenated salicylanilide, or a pharmaceutically acceptable salt or ester thereof (for example rafoxanide), for use in a method of preventing or inhibiting recurrence of *C. difficile* infection in a subject with a *C. difficile* infection, the method comprising administering the halogenated salicylanilide, or a pharmaceutically acceptable salt or ester thereof to the subject.

Halogenated Salicylanilides

Halogenated salicylanilides are also known as 2-hydroxy-N-phenylbenzamides or 2-hydroxybenzanilides. Salicylanilides are weakly acidic phenolic compounds. Halogenated salicylanilides are salicylanilides substituted by at least one halo group. The compounds were originally developed as fungicides for topical use and as antimicrobial agents in soaps. Later these compounds were shown to possess potent antihelmintic activity of which niclosamide, tribromosalan and clioxanide were some of the first agents to be used. A wide range of halogenated salicylanilide derivatives are known. Any halogenated salicylanilide possessing antibacterial activity against *Clostridium* may be used in the present invention. For example, the halogenated salicylanilide may be any of the niclosamide analogues described in WO 2008/021088, which are incorporated herein by reference thereto.

The halogenated salicylanilide may be a halogenated salicylanilide of the formula (I):

(I)

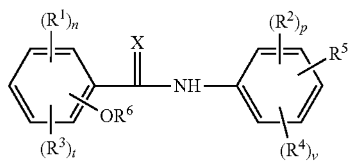

wherein

X is O or S;

$R^1$ and $R^2$ are at each occurrence independently selected from halo;

$R^3$ and $R^4$ are at each occurrence independently selected from H, $C_{1-6}$ alkyl, $—OR^{A1}$, $—NO_2$ and —CN;

$R^5$ is H or $-L^1-R^7$;

$R^6$ is H or $—C(O)R^{A2}$;

$L^1$ is selected from a bond, O, S, or $—(CR^{A3}R^B)_o—$, wherein o is 1 or 2;

$R^6$ is phenyl, unsubstituted or substituted with 1, 2, or 3 groups selected from halo, $C_{1-4}$ alkyl, $—OR^{A4}$, $—NO_2$ and —CN;

$R^{A1}$, $R^{A2}$, $R^{A3}$ and $R^{A4}$ are at each occurrence independently selected from H and $C_{1-4}$ alkyl;

$R^B$ is at each occurrence selected from H, $C_{1-4}$ alkyl and —CN;

n and p are each independently selected from 0, 1, 2, 3 or 4, with the proviso that n+p is at least 1;

t and v are independently selected from 0, 1 and 2;

or a pharmaceutically acceptable salt, or ester thereof.

The halogenated salicylanilide of formula (I) may be of the formula (II), or a pharmaceutically acceptable salt, or ester thereof.

(II)

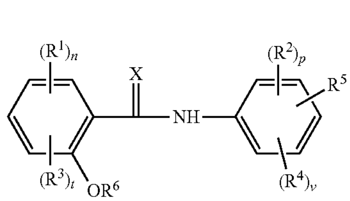

The following statements in the numbered paragraphs below apply to compounds of the formulae (I) or (II). These statements are independent and interchangeable. In other words, any of the features described in any one of the following statements may (where chemically allowable) be combined with the features described in one or more other statements below. In particular, where a compound is exemplified or illustrated in this specification, any two or more of the statements below which describe a feature of that compound, expressed at any level of generality, may be combined so as to represent subject matter which is contemplated as forming part of the disclosure of this invention in this specification.

1. X is O.

2. $R^1$ and $R^2$ are at each occurrence independently selected from fluoro, chloro, bromo and iodo.

3. $R^1$ and $R^2$ are at each occurrence independently selected from chloro, bromo and iodo.

4. $R^1$ is chloro.

5. $R^1$ is bromo.

6. $R^1$ is iodo.

7. $R^2$ is chloro.

8. $R^2$ is bromo.

9. $R^2$ is iodo.

10. $R^3$ and $R^4$ are at each occurrence independently selected from H, $C_{1-4}$ alkyl, $—OR^{A1}$, $—NO_2$ and —CN.

11. $R^3$ and $R^4$ are at each occurrence independently selected from H, $C_{1-4}$ alkyl, $—OR^{A1}$ and $—NO_2$.

12. $R^3$ and $R^4$ are at each occurrence independently selected from H, $C_{1-4}$ alkyl, —OH, —OMe, $—NO_2$ and —CN, for example H, $C_{1-4}$ alkyl, —OH or $—NO_2$.

13. $R^5$ is H.

14. $R^5$ is $-L^1-R^7$.

15. $L^1$ is selected from —O—, $—CH_2—$ and —CH(CN)—, for example —O— or —CH(CN)—.

16. $R^7$ is phenyl, unsubstituted or substituted with 1, 2, or 3 groups selected from halo, $C_{1-4}$ alkyl and —CN 17. $R^7$ is phenyl unsubstituted or substituted with 1, 2, or 3 groups (for example 1 or 2 groups) selected from halo.

18. $R^7$ is unsubstituted phenyl.

19. $L^1$ is selected from —O— and —CH(CN)—; and $R^7$ is phenyl unsubstituted or substituted with 1, 2, or 3 groups selected from halo.

20. $R^6$ is H.

21. $R^6$ is $—C(O)R^{A2}$, for example $—C(O)CH_3$.

22. t=0 or 1.

23 t=0.

24. v=0 or 1.

25. v=0.

26. o is 1.

27. v=1 and $R^4$ is selected from —OH, $C_{1-4}$ alkyl and $—NO_2$.

28. A compound of any of formulae (I) or (II), or a pharmaceutically acceptable salt thereof.

Particular compounds are compounds of formula (I) or formula (II), or a pharmaceutically acceptable salt or ester thereof wherein:

X is O;

$R^1$ and $R^2$ are at each occurrence independently selected from halo;

$R^3$ and $R^4$ are at each occurrence independently selected from H, $C_{1-4}$ alkyl, $—OR^{A1}$, $—NO_2$ and CN;

$R^5$ is H or $-L^1-R^7$;

$R^6$ is H or $—C(O)R^{A2}$;

$L^1$ is selected from O and —CH(CN)—;

$R^7$ is phenyl unsubstituted or substituted with 1, 2, or 3 groups selected from halo;

$R^{A1}$ and $R^{A2}$ are at each occurrence independently selected from H and $C_{1-4}$ alkyl;

n and p are each independently selected from 0, 1, 2, 3 or 4, with the proviso that n+p is at least 1;

t and v are independently selected from 0, 1 and 2.

or a pharmaceutically acceptable salt, or ester thereof.

The halogenated salicylanilide may be selected from:

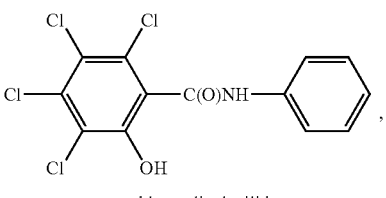

tetrachlorosalicylanilide

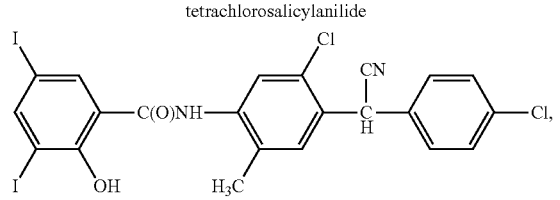

closantel

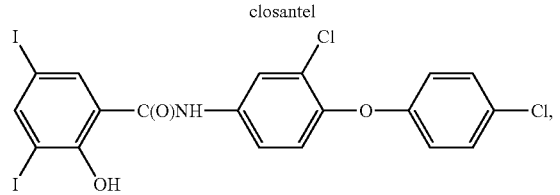

rafoxanide

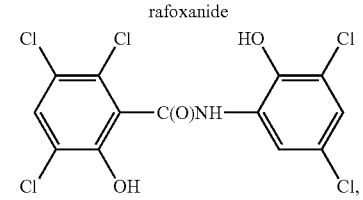

oxyclosanide

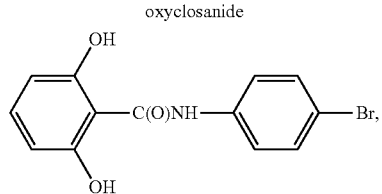

resorantel

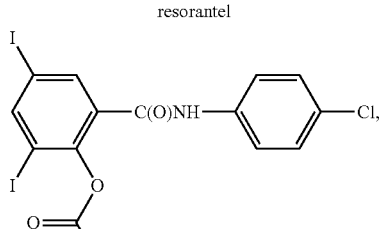

clioxanide

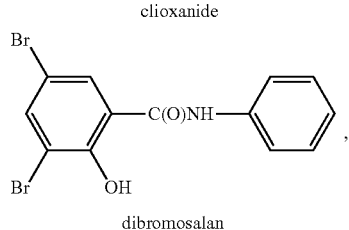

dibromosalan

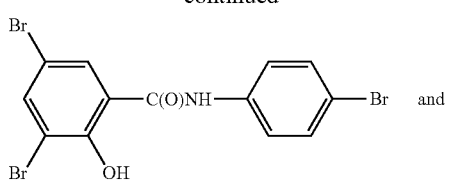 and tribromosalan

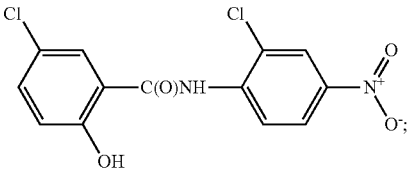

niclosamide or a pharmaceutically acceptable salt or ester thereof.

The halogenated salicylanilide may be:

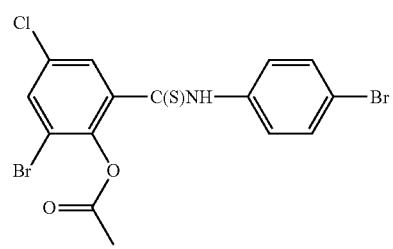

brotianide or a pharmaceutically acceptable salt or ester thereof.

The halogenated salicylanilide may be a compound selected from Table 1 in WO 2008/021088, or a pharmaceutically acceptable salt thereof.

It may be that the halogenated salicylanilide, for example the halogenated salicylanilide of the formulae (I) or (II) is not the following compounds:

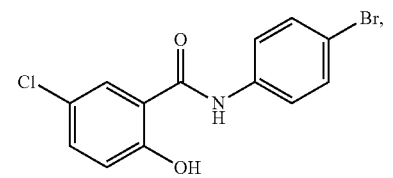

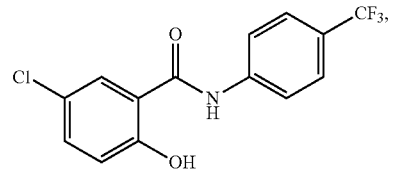

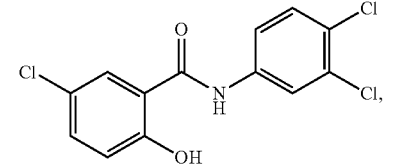

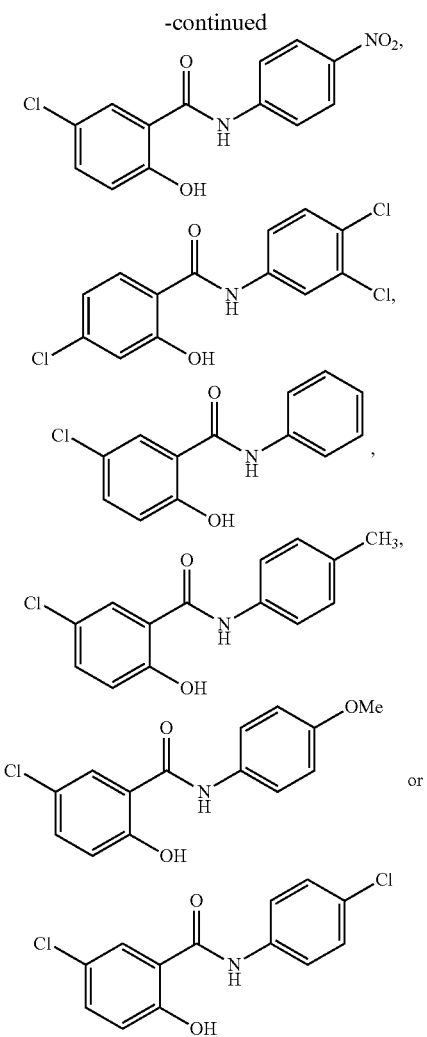

The halogenated salicylanilide may be selected from the group consisting of tetrachlorosalicylanilide, closantel, rafoxanide, oxyclozanide, resorantel, clioxanide, dibromosalan, tribromosalan, brotianide and niclosamide, or a pharmaceutically acceptable salt or ester thereof.

The halogenated salicylanilide may be selected from the group consisting of tetrachlorosalicylanilide, closantel, rafoxanide, oxyclozanide, resorantel, dibromosalan, tribromosalan and niclosamide, or a pharmaceutically acceptable salt or ester thereof.

The halogenated salicylanilide may be selected from the group consisting of clioxanide, closantel, oxyclozanide, rafoxanide, tribromosalan or a pharmaceutically acceptable salt or ester thereof.

The halogenated salicylanilide may be selected from the group consisting of tetrachlorosalicylanilide, closantel, rafoxanide, oxyclozanide, resorantel, clioxanide, dibromosalan, tribromosalan, brotianide and niclosamide, or a pharmaceutically acceptable salt thereof.

The halogenated salicylanilide may be selected from the group consisting of tetrachlorosalicylanilide, closantel, rafoxanide, oxyclozanide, resorantel, clioxanide, dibromosalan, tribromosalan and niclosamide, or a pharmaceutically acceptable salt thereof.

The halogenated salicylanilide may be selected from the group consisting of niclosamide, clioxanide, closantel, oxyclozanide, rafoxanide and tribromosalan, or a pharmaceutically acceptable salt thereof.

The halogenated salicylanilide may be selected from the group consisting of clioxanide, closantel, oxyclozanide, rafoxanide and tribromosalan, or a pharmaceutically acceptable salt thereof.

The halogenated salicylanilide may be selected from the group consisting of rafoxanide, oxyclozanide and clioxanide, or a pharmaceutically acceptable salt thereof.

The halogenated salicylanilide may be selected from the group consisting of clioxanide, closantel, rafoxanide and tribromosalan, or a pharmaceutically acceptable salt thereof.

The halogenated salicylanilide may be selected from the group consisting of tetrachlorosalicylanilide, closantel, rafoxanide, oxyclozanide, resorantel, clioxanide, dibromosalan, tribromosalan, brotianide and niclosamide.

The halogenated salicylanilide may be niclosamide, or a pharmaceutically acceptable salt or ester thereof, for example the halogenated salicylanilide is niclosamide or a pharmaceutically acceptable salt thereof, suitably the halogenated salicylanilide is niclosamide.

The halogenated salicylanilide may be clioxanide, or a pharmaceutically acceptable salt or ester thereof, for example the halogenated salicylanilide is clioxanide or a pharmaceutically acceptable salt thereof, suitably the halogenated salicylanilide is clioxanide.

The halogenated salicylanilide may be closantel, or a pharmaceutically acceptable salt or ester thereof, for example the halogenated salicylanilide is closantel or a pharmaceutically acceptable salt thereof, suitably the halogenated salicylanilide is closantel.

The halogenated salicylanilide may be oxyclozanide, or a pharmaceutically acceptable salt or ester thereof, for example the halogenated salicylanilide is oxyclozanide or a pharmaceutically acceptable salt thereof, suitably the halogenated salicylanilide is oxyclozanide.

The halogenated salicylanilide may be rafoxanide, or a pharmaceutically acceptable salt or ester thereof, for example the halogenated salicylanilide is rafoxanide or a pharmaceutically acceptable salt thereof, suitably the halogenated salicylanilide is rafoxanide.

The halogenated salicylanilide may be tribromosalan, or a pharmaceutically acceptable salt or ester thereof, for example the halogenated salicylanilide is tribromosalan or a pharmaceutically acceptable salt thereof, suitably particularly the halogenated salicylanilide is tribromosalan.

It is to be understood that any of the halogenated salicylanilides described in this section or elsewhere in the application may be used in any of the treatments described herein.

The halogenated salicylanilide may be administered to the subject using any suitable route, for example parenterally (for example intravenous, intramuscular or subcutaneous administration), mucosal administration (for example oral or rectal administration. Suitably the halogenated salicylanilide is administered orally or rectally. More particularly the halogenated salicylanilide is administered orally.

The subject or patient in any of the treatments described is suitably a human or animal, for example a warm-blooded animal. Particularly the subject is a human. The subject may be a human aged 65 years or older. The subject may be an animal, e.g. a mammal. In particular, the halogenated salicylanilide may be for use in the treatment of *Clostridium* infections in commercial animals such as livestock (e.g. cows, sheep, chickens, pigs, geese, ducks, goats, etc.). Alternatively, halogenated salicylanilide can be used to treat companion animals such as cats, dogs, horses, etc. The treatment of animals infected a *C. difficile* with may be particularly effective for preventing spread of infection through animal fecal matter to humans or other animals.

Also provided is the use a halogenated salicylanilide, or a pharmaceutically acceptable salt or ester thereof for the manufacture of a medicament for the treatment of an infection in a subject caused by *Clostridium* bacteria.

Also provided is a method of treating an infection caused by *Clostridium* bacteria in a subject, the method comprising administering to said subject a therapeutically effective amount of a halogenated salicylanilide, or a pharmaceutically acceptable salt or ester thereof.

It is to be understood that the use and methods of the above two paragraphs are applicable to any of the infections, halogenated salicylanilides and routes of administration described herein.

Preferred, suitable, and optional features of any one particular aspect of the present invention are also preferred, suitable, and optional features of any other aspect.

BRIEF DESCRIPTION OF THE DRAWINGS

FIG. 1 shows the development of heat-resistant spore count over time for *Clostridium difficile* 7-6011209 in the presence of rafoxanide or fidaxomicin at a concentration of 8-fold above the MIC for rafoxanide and >8-fold above the MIC for fidaxomicin. The control shows the spore count over time in the Clospore medium used in the study.

DETAILED DESCRIPTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a subject, for example a human, that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms. Accordingly in the context of treating infections caused by a *Clostridium* bacteria includes:
(i) the prevention of a disease caused by *Clostridium* species, particularly *Clostridium difficile*;
(ii) the suppression of a disease caused by *Clostridium* species, particularly *Clostridium difficile*;
(iii) the relief of symptoms of a disease caused by *Clostridium* species, particularly *Clostridium difficile*;
iv) the eradication of a non-symptomatic colonization by *Clostridium* species, particularly *Clostridium difficile* from an area on or in the body;
(v) the eradication of a *Clostridium difficile* symptomatic infection;
(vi) the eradication a *Clostridium* species, particularly *Clostridium difficile*; from an area of the body affected by another disease that could enable establishment of an infection more readily, than in a non-disease affected area—e.g. in the intestinal tract;
(vii) the suppression of a disease caused a *Clostridium* infection, particularly *Clostridium difficile*; from an area of the body affected by another noninfectious disease that enables establishment of an infection more readily, than in a non-disease affected area;
(viii) preventing or reducing the risk of transmission or spread of a *Clostridium* infection, particularly *Clostridium difficile*; or
(ix) preventing or reducing the risk of recurrence of a *Clostridium* infection, particularly *Clostridium difficile*.

A "therapeutically effective amount" means the amount of a compound that, when administered to a subject, for example a human, for treating a disease, is sufficient to effect such treatment for the disease. The "therapeutically effective amount" will vary depending on the compound, the disease and its severity and the age, weight, etc., of the subject to be treated.

Minimum inhibitory concentration (MIC) is the lowest concentration of an antibacterial that will inhibit the visible growth of a microorganism after overnight incubation. Minimum inhibitory concentrations are important in diagnostic laboratories to confirm resistance of microorganisms to an antimicrobial agent and also to monitor the activity of new antimicrobial agents. A MIC is generally regarded as the most basic laboratory measurement of the activity of an antimicrobial agent against an organism.

The median lethal dose, LD50 (abbreviation for "lethal dose, 50%") of a toxin, radiation, or pathogen is the dose required to kill half the members of a tested population after a specified test duration. LD50 figures are frequently used as a general indicator of a substance's acute toxicity.

Therapeutic index (therapeutic ratio) is defined as the amount of a therapeutic agent causing the therapeutic effect measured as MIC to the amount that causes death in animal studies measured as LD50.

The rate of resistance development is quantified as the frequency of spontaneous mutants in a population of bacteria that is able to resist a given concentration of an antibiotic. For example the rate of resistance development may be $10^{-9}$ if on average 1 cell in $10^9$ cells is able to survive a concentration of antibiotic corresponding to 1×MIC incubated at 37° C. for 48 hours using the method described in Drago et al. Journal of Antimicrobial Chemotherapy, 2005, 56(2), 353 to 359).

In microbiology, colony-forming unit (CFU) is an estimate of the number of viable bacteria or fungal cells in a sample. Viable is defined as the ability to multiply via binary fission under the controlled conditions.

The term "halo" or "halogen" refers to one of the halogens, group 17 of the periodic table. In particular the term refers to fluorine, chlorine, bromine and iodine.

The term $C_m$-$C_n$ refers to a group with m to n carbon atoms.

The term "$C_1$-$C_6$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. "$C_1$-$C_4$ alkyl" similarly refers to such groups containing up to 4 carbon atoms.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without undue effort which substitutions are chemically possible and which are not.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Suitable or preferred features of any compounds of the present invention may also be suitable features of any other aspect.

The invention contemplates pharmaceutically acceptable salts of the halogenated salicylanilide compounds of the invention. These may include the acid addition and base salts of the compounds. These may be acid addition and base salts of the compounds. Suitable acid addition salts are formed from acids which form non-toxic salts. Suitable base salts are formed from bases which form non-toxic salts.

Pharmaceutically acceptable salts of the halogenated salicylanilide compounds may be prepared by for example, one or more of the following methods:
(i) by reacting the compound of the invention with the desired acid or base; or
(ii) by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Where a compound of the invention has two or more stereocentres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diasteroemeric mixtures. Where the mixture is a mixture of enantiomers the enantiomeric excess may be any of those disclosed above. Where the compound is a single stereoisomer the compounds may still contain other diasteroisomers or enantiomers as impurities. Hence a single stereoisomer does not necessarily have an enantiomeric excess (e.e.) or diastereomeric excess (d.e.) of 100% but could have an e.e. or d.e. of about at least 85%

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess activity against *Clostridium* bacteria, for example *C. difficile*.

It is also to be understood that certain compounds of the invention, or salts or esters thereof, may exist in solvated as well as unsolvated forms such as, for example, hydrated forms. It is to be understood that the invention encompasses all such solvated forms that possess activity against *Clostridium* bacteria, for example *C. difficile*.

It is also to be understood that the halogenated salicylanilides of the invention may exhibit polymorphism, and that the invention encompasses all such forms that possess activity against *Clostridium* bacteria, for example *C. difficile*.

It is further to be understood that the halogenated salicylanilide may be used in the form of suitable pharmaceutically-acceptable pro-drug of the compound and that such prodrugs are intended to be encompassed by the invention. Accordingly, halogenated salicylanilide may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a hydroxy group in a compound.

Accordingly, the present invention includes the halogenated salicylanilides as defined hereinbefore when made available by organic synthesis and when made available within the human or animal body by way of cleavage of a pro-drug thereof. Accordingly, the present invention includes those halogenated salicylanilide compounds that are produced by organic synthetic means and also such compounds that are produced in the human or animal body by way of metabolism of a precursor compound, that is the halogenated salicylanilide may be a synthetically-produced compound or a metabolically-produced compound.

A suitable pharmaceutically-acceptable pro-drug of a halogenated salicylanilide compound is one that is based on reasonable medical judgement as being suitable for administration to the human or animal body without undesirable pharmacological activities and without undue toxicity.

Various forms of pro-drug have been described, for example in the following documents:— a) Methods in Enzymology, Vol. 42, p. 309-396, edited by K. Widder, et a/. (Academic Press, 1985);

b) Design of Pro-drugs, edited by H. Bundgaard, (Elsevier, 1985);

c) A Textbook of Drug Design and Development, edited by Krogsgaard-Larsen and

H. Bundgaard, Chapter 5 "Design and Application of Prodrugs", by H. Bundgaard p. 113-191 (1991);

d) H. Bundgaard, *Advanced Drug Delivery Reviews,* 8, 1-38 (1992);

e) H. Bundgaard, et al., *Journal of Pharmaceutical Sciences,* 77, 285 (1988);

f) N. Kakeya, et al., *Chem. Pharm. Bull.,* 32, 692 (1984);

g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

The halogenated salicylanilide may be used in the form of a prodrug of the compound for example, an in vivo cleavable ester thereof. An in vivo cleavable ester of a compound may be, for example, a pharmaceutically-acceptable ester which is cleaved in the human or animal body to produce the parent compound.

A suitable pharmaceutically-acceptable pro-drug of a halogenated salicylanilide that possesses a hydroxy group is, for example, an in vivo cleavable ester or ether thereof. An in vivo cleavable ester or ether of a compound containing a hydroxy group is, for example, a pharmaceutically-acceptable ester or ether which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically-acceptable ether forming groups for a hydroxy group include α-acyloxyalkyl groups such as acetoxymethyl and pivaloyloxymethyl groups. Accordingly reference to a "pharmaceutically acceptable ester" of a compound encompasses the esters described above.

Halogenated Salicylanilides

The halogenated salicylanilide used in the present invention may be any of the halogenated salicylanilides described herein, or a pharmaceutically acceptable salt thereof, or a pharmaceutically acceptable sat thereof, or a pro-drug of any thereof.

Particular halogenated salicylanilides include the compounds of formulae (I) and (II) or a pharmaceutically acceptable salt thereof as described herein.

More particularly the halogenated salicylanilide is selected from the group consisting of tetrachlorosalicylanilide, closantel, rafoxanide, oxyclozanide, resorantel, clioxanide, dibromosalan, tribromosalan and niclosamide.

Niclosamide

In a one embodiment of the invention the halogenated salicylanilide is niclosamide or a pharmaceutically acceptable salt thereof. Niclosamide (2',5-dichloro-4'-nitrosalicylanilide) exhibits the following acute toxicity:

$LD_{50}$, mice, p.o., >5000 mg/kg $LD_{50}$, rats, p.o., 5000 mg/kg $LD_{50}$, rats, dermal, 2000 mg/kg $LD_{50}$, rabbits, p.o., 5000 mg/kg $LD_{50}$, cats, p.o., >1000 mg/kg Niclosamide thus exhibits low toxicity. The compound is poorly soluble in water and shows low intestinal absorption. Once in the bloodstream niclosamide is quickly cleared via the urinary tract or by enzymatic metabolism in the liver.

Niclosamide Derivatives

It is believed that a number of niclosamide analogs will act in a manner similar to niclosamide in the treatment of the *Clostridium* infections described herein. Illustrative niclosamide analogs include, but are not limited to closantel (CAS #: 57808-65-8), oxyclozanide (CAS #: 2277-92-1), rafoxanide (CAS #: 22662-39-1), clioxanide (CAS #: 14437-41-3). Other suitable niclosamide analogs include brotianide (CAS #: 23233-88-7), 4'-chloro-3-nitrosalicylanilide, 4'-chloro-5-nitrosalicylanilide, 2'-chloro-5'-methoxy-3-nitrosalicylanilide, 2'-methoxy-3,4'-dinitrosalicylanilide, 2',4'-dimethyl-3-nitrosalicylanilide, 2'-chloro-3,4'-dinitrosalicylanilide, 2'-ethyl-3-nitrosalicylanilide and 2'-bromo-3-nitrosalicylanilide; or a pharmaceutically acceptable salt thereof. Further niclosamide derivatives include those described in WO 20081021088, particularly those described in Table 1 therein, which are incorporated herein by reference.

Particular niclosamide analogues include closantel, rafoxanide and oxyclozanide. These compounds are expected to have a suitable toxicity profile for the use described herein.

Acute toxicity of closantel:

$LD_{50}$, rats, p.o., 262-342 mg/kg (depending on the study), median 302 mg/kg $LD_{50}$, rats, s.c., 67 mg/kg $LD_{50}$, mice, p.o., 331 mg/kg $LD_{50}$, mice, i.m., 57 mg/kg Acute toxicity of rafoxanide:

$LD_{50}$, rats, p.o., 980→2000 mg/kg (depending on the study), median>1490 mg/kg $LD_{50}$, mice, p.o., 232-300 mg/kg (depending on the study), median 266 mg/kg $LD_{50}$, rabbits, p.o., 3200 mg/kg Acute toxicity of oxyclozanide.

$LD_{50}$, rats, p.o., 980-3519 mg/kg (depending on the study), median 2250 mg/kg $LD_{50}$, mice, p.o., 300 mg/kg $LD_{50}$, rabbits, p.o., 3200 mg/kg Brominated Halogenated Salicylanilides In another embodiment the halogenated salicylanilide is a brominated halogenated salicylanilide, for example 4',5-dibromosalicylanilide (also known as dibromsalan); 3,5-dibromosalicylanilide (also known as metabromsalan; and 3,4',5-tribromosalicylanilide (also known as tribromsalan).

Synthesis

The halogenated salicylanilides described herein are known or can be synthesised using known methods. For example using methods analogous to those described in WO2004/006906. The compounds of the Formula (I) herein may be prepared by coupling an amine of the formula (III) with an acid of formula (IV):

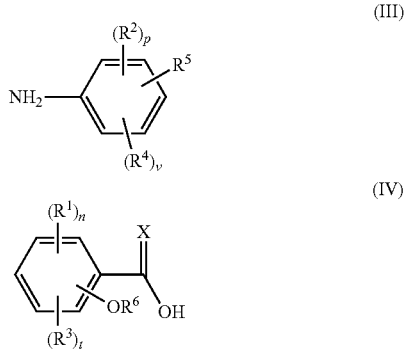

Necessary starting materials are known or can be prepared using standard procedures of organic chemistry.

Pharmaceutical Compositions

The halogenated salicylanilide may be administered to the subject in the form of a pharmaceutical composition comprising the halogenated salicylanilide, or a pharmaceutically acceptable salt or ester thereof, and a pharmaceutically acceptable excipient.

Conventional procedures for the selection and preparation of suitable pharmaceutical formulations are described in, for example, "Pharmaceuticals—The Science of Dosage Form Designs", M. E. Aulton, Churchill Livingstone, 1988.

The composition may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intraperitoneal dosing or as a suppository for rectal dosing). Suitably the composition is in a form suitable for oral administration.

The compositions may be obtained by conventional procedures using conventional pharmaceutical excipients, well known in the art. Thus, compositions intended for oral use may contain, for example, one or more colouring, sweetening, flavouring and/or preservative agents.

Dosage

The amount of active ingredient that is combined with one or more excipients to produce a single dosage form will necessarily vary depending upon the subject treated and the particular route of administration. For example, a formulation in a unit dose form such as a tablet or capsule intended for oral administration to humans will generally contain, for example, from 0.1 mg to 5 mg, for example from 0.5 mg to 5 g, from 0.5 to 1000 mg or from 10 to 500 mg of the halogenated salicylanilide compounded with an appropriate and convenient amount of excipients which may vary from about 5 to about 98 percent by weight of the total composition.

The size of the dose of the halogenated salicylanilide for the treatment of the *Clostridium* infections described herein will naturally vary according to the nature and severity of the conditions, the age and sex of the animal or patient and the route of administration, according to well-known principles of medicine.

The halogenated salicylanilide will generally be administered in a dose of about 0.001 to about 75 mg/kg, for example from about 0.013 to about 66.7 mg/kg, about 0.5 to about 30 mg/kg or from about 2.5 to about 30 mg/kg. The halogenated salicylanilide may be administered within these dosage ranges to the subject from 1 to 4 times per day. The dosage may be administered by any suitable route, for example parenterally, orally or rectally. A particular route of administration which is generally applicable to all of the uses of the halogenated salicylanilides described herein is the oral administration of the halogenated salicylanilide to the subject.

The particular dosage regimen used to treat a subject will depend on a number of factors that may readily be determined, such as the severity of the condition and its responsiveness to initial treatment, but will normally involve one or more administrations per day on an ongoing basis. The effective dosage of the pharmaceutical composition of the present invention varies from the formulation, administration pathway, age, weight and gender of a human or animal or with a disease caused by *Clostridium* species, particularly *Clostridium difficile* colonizing or infecting the intestinal tract of a human or animal having a *Clostridium difficile* infection.

Therapeutic Use

As described hereinbefore the halogenated salicylanilide is used for the treatment of an infection caused by *Clostridium* bacteria, particularly *C. difficile*. The halogenated salicylanilide may act to kill or eradicate the infection from the subject, thus providing a bactericidal effect. Alternatively the halogenated salicylanilide may inhibit growth or replication of the bacteria thus producing a bacteriostatic effect. In the context of the present invention, treatment of a condition encompasses both therapeutic and prophylactic treatment, of either an infectious or a non-infectious condition, in a subject for example a mammal such as a human or animal, but in particular a human. It may involve complete or partial eradication of the condition, removal or amelioration of associated symptoms, arresting subsequent development of the condition, and/or prevention of, or reduction of risk of, subsequent occurrence of the condition.

Generally the halogenated salicylanilide will be administered to a subject experiencing symptoms of a *Clostridium* infection (for example a *C. difficile* infection). Accordingly, the halogenated salicylanilide may be for use in the treatment of a *C. difficile* associated disease, for example the halogenated salicylanilide may be for use in the treatment of a *C. difficile* associated disease selected from diarrhoea and colitis (including pseudomembranous colitis.

In an alternative embodiment the halogenated salicylanilide is for use in the treatment of a *C. difficile* in a subject, wherein the subject is asymptomatic. Such uses may be useful to eradicate or inhibit a *C. difficile* infection in a subject that is at risk of developing *C. difficile* associated disease. Such subjects could include, for example subjects which require surgical procedures in which prophylactic antibiotics may be administered (for example certain orthopaedic surgery). By eradicating the *C. difficile* infection prior to administration of further antibiotics, the risk of antibiotic induced diarrhoea may be reduced.

Subjects who have previously suffered from an antibiotic induced *C. difficile* infection may be at a particular risk of developing a *C. difficile* infection if they are administered antibiotics in the future. Accordingly, in another embodiment the halogenated salicylanilide is for use in the treatment of a subject prior to the administration of an antibiotic other than the halogenated salicylanilide, wherein the patient is asymptomatic of a *C. difficile* infection prior to administration of the halogenated salicylanilide and where the subject has previously suffered from an antibiotic induced a *C. difficile* infection.

When the *Clostridium* infection is an antibiotic induced *Clostridium* infection (for example a *C. difficile* infection) further administration of the antibiotic causing the induced infection is suitably halted. Alternatively, the dosage of the antibiotic may be reduced or gradually tapered so as to reduce the risk of exacerbating the antibiotic induced *Clostridium* infection. Accordingly the halogenated salicylanilide may be administered to the subject concurrently with another antibiotic being used to treat a primary infection in the subject. For example it may be that the halogenated salicylanilide is administered to the subject concurrently with an antibiotic being used to treat a primary infection other than a *C. difficile* infection. The antibiotic used to treat the primary infection may, for example, be one or more antibiotics selected from a penicillin, a cephalosporin, a carbapenem, a monobactam (for example a β-lactam antibiotic), a fusidane, a fluoroquinolone, a tetracycline, a glycylcycline, phenicol (for example chloramphenicol), a macrolide, a macrocyclic (for example fidaxomicin), a rifamycin, a ketolide, a lincosamide, an oxazolidinone, an aminocyclitol, a polymyxin, a glycopeptide, an aminoglycoside, a lipopeptide, an antimycobacterial, a nitromidazole, bacitracin, mupiricin, a pleuromutilin, a rifamycin, a sulphonamide and trimethoprim, or a combination of two or more thereof. However, preferably the halogenated salicylanilide is used alone or together with a reduced or tapered dose of the antibiotic(s) responsible for the induced *Clostridium* infection. More preferably the halogenated salicylanilide is administered to the subject in the absence of any other antibiotic.

In one embodiment the halogenated salicylanilide is administered to the subject concurrently with another therapeutic agent in any of the treatments of the *Clostridium* infections (particularly the *C. difficile*) infections described herein. The other therapeutic agent may be, for example, an antibiotic active against *C. difficile*, a microbiome therapeutic or faecal transplant, or a vaccine or an antibody therapy for e.g. *C. difficile*.

Accordingly in may be that the halogenated salicylanilide is administered to the subject concurrently with another antibiotic active against a *Clostridium* infection, particularly a *C. difficile* infection, other than the halogenated salicylanilide itself. Examples of such antibiotics include a nitroimidazole, for example metronidazole; a benzimidazole, for example ridinilazole (SMT19969); a glycopeptide, for example vancomycin; a macrocyclic antibiotic, for example fidaxomicin; an oxazolidinone, for example cadazolid; a lipopeptide, for example surothromycin or daptomycin; a glycylcycline, for example tigecycline; a DNA Minor Groove Binder (for example MGB-BP-3) a glycolipodepsipeptide (for example ramoplanin); CRS3123 (a Methionyl-tRNA synthetase (MetRS) inhibitor, Crestone Inc); and a rifamycin such as rifaximin, or a combination of two or more thereof. It may be that the halogenated salicylanilide is administered concurrently with metronidazole (for example concurrently with intravenous metronidazole).

It may be that the halogenated salicylanilide is administered to the subject concurrently with a vaccine, for example concurrently with a vaccine which induces an immune response to *C. difficile* toxins, for example toxins A and B (e.g. ACAM-CDIFF, Sanofi, or VLA84 (a fusion protein containing cell binding domains of Toxins A and B, Valneva), or a vaccine which prevents a *C. difficile* infection, for example PF06425090 (Pfizer).

It may be that the halogenated salicylanilide is administered to the subject concurrently with an antibody therapeutic, for example actoxumab and bezlotoxumab or a combination thereof.

It may be that the halogenated salicylanilide is administered to the subject concurrently with a faecal transplantation or microbiome therapeutics, for example concurrently with a faecal transplant, spores from a non-toxigenic *C. difficile* strain (e.g. VP-20621); spores from microbiome organisms (e.g. SER-109), a microbiota suspension (e.g. RBX2660), a probiotic (e.g. *lactobacillus* reuterei) or a β-lactamase, for example SYN-004.

Reference to administration "concurrently" herein includes the separate, simultaneous or separate administration of the halogenated salicylanilide with the other therapy. The halogenated salicylanilide may be administered to the subject administered by the same or different routes of administration, for example oral, intravenously, subcutaneously, or rectally). The halogenated salicylanilide and the other therapy may be administered as a combined preparation; however, generally they will be administered as separate dosage forms to enable the dose and dosing regimen of each to be tailored accordingly.

The presence of a *Clostridium* infection (for example a *C. difficile* infection) in a subject may be diagnosed using convention methods, for example infection may be suspected from subject exhibiting symptoms of a *C. difficile* associated disease. Infection may also be diagnosed using known methods for example A complete blood count to test for the presence of leukocytosis Measurement of albumin levels to check for hypoalbuminemia, which may accompany severe disease.

Testing for elevated serum lactate levels (5 mmol/L), which can be a sign of severe disease.

Stool examination. Stools may be positive for blood in severe colitis. Faecal leukocytes are present in about half of cases.

Stool assays for *C. difficile*, may also be used including the following:

Stool culture: This is a sensitive test. However, the results are slow and may lead to a delay in the diagnosis.

Glutamate dehydrogenase enzyme immunoassay (EIA): This is a very sensitive test and detects the presence of glutamate dehydrogenase produced by C. difficile.

Real-time polymerase chain reaction (PCR) assay: This test is an alternative "gold standard" to stool culture. The assay may be used to detect the C. difficile gene toxins.

EIA for detecting toxins A and B produced by C. difficile.

Imaging studies and procedures may also be used to detect infection in a subject. Suitable methods include abdominal computed tomography (CT) scanning. This method is particularly suitable when pseudomembranous colitis or other complications of CDI are suspected. In subjects with sepsis due to suspected megacolon, abdominal radiography may be performed instead of CT scanning to establish the presence of megacolon.

The use of halogenated salicylanilides for the treatment of a Clostridium infection (for example a C. difficile infection) as described herein is expected to provide a wider therapeutic window than conventional treatments such as vancomycin, metronidazole or fidaxomicin. Accordingly, the use of halogenated salicylanilides may result in reduced side effects compared to known C. difficile treatments.

Halogenated salicylanilides (e.g. niclosamide) are poorly absorbed following oral administration. Accordingly, the concentration of the halogenated salicylanilide in the faeces is expected to be high compared to for example oral administration of similar doses of vancomycin or metronidazole. A high local concentration of the halogenated salicylanilide in the GI tract, especially the colon, would be expected to enhance the potency and or efficiency of the antibacterial effect locally in the intestine and colon.

As illustrated in the examples, a number of the halogenated salicylanilide tested had similar or higher potencies than vancomycin, metronidazole or fidaxomicin and may therefore be expected to provide an antibacterial effect on Clostridium infections at a similar or lower dose than conventional treatments such as vancomycin.

Clostridium bacteria (for example C. difficile) are expected to exhibit a low frequency of spontaneous mutation in the presence of the halogenated salicylanilides described herein. Therefore, it is expected that the risk of resistance to the halogenated salicylanilide emerging will be low.

EXAMPLES

In the examples below, the effects of various halogenated salicylanilides are compared to vancomycin (a currently approved compound for the treatment Clostridium difficile infections).

Example 1 MIC Determinations

C. difficile MICs are determined according to CLSI guideline using microbroth dilution as described in "Methods for Antimicrobial Susceptibility Testing of Anaerobic Bacteria; Approved Standard—Eighth Edition" CLSI, ISBN: 1-56238-789-8", except isovitalex was used in the place of lysed horse blood.

The media used for the C. difficile MIC tests was Brucella broth supplemented with hemin (5 pg/ml), vitamin K and Isovitalex (according to the manufacturer's instructions). Inoculated plates were incubated for 44 to 48 hours at 36° C. under anaerobic conditions (anaerobic chamber or anaerobic jar with gaspack).

The C. difficile strain ATCC 700057 was used as a reference control during the C. difficile MIC determinations. This strain has an expected MIC towards vancomycin of 1 ug/mL.

The results are shown in Tables 2 and 3.

TABLE 2

MIC of clinical isolates of C. difficile against niclosamide and vancomycin

| C. difficile isolate | Niclosamide (ug/mL) | Vancomycin (ug/mL) |
|---|---|---|
| 7-6011209 | 0.06 | 0.5 |
| 7-7150288 | 0.125 | 1 |
| 7-7152701 | 0.25 | 2 |
| 7-7154992 | 0.25 | 1 |
| 7-5779928 | 0.25 | 2 |
| 7-6778909 | 0.25 | 0.5 |
| 7-6870430 | 0.25 | 0.5 |
| 7-7154712 | 0.25 | 2 |
| 7-7104022 | 0.125 | 1 |
| 7-7153872 | 0.5 | 2 |
| 7-5085357 | 0.125 | 0.5 |
| 7-7150997 | 0.125 | 0.5 |
| 7-6008526 | 0.25 | 2 |
| 7-7124449 | 0.125 | 0.5 |
| 7-6854508 | 0.125 | 0.5 |
| 7-7363761 | 0.125 | 0.5 |
| 7-7200552 | 0.25 | 0.5 |
| 7-7150318 | 0.125 | 0.5 |
| 7-7150628 | 0.125 | 1 |
| 7-7149204 | 0.125 | 1 |
| 7-7154712 | 0.25 | 2 |
| 7-7116411 | 0.125 | 2 |
| 7-7151551 | 0.25 | 2 |
| 7-7156197 | 0.25 | 2 |
| 12055 | 0.125 | 0.5 |
| 12060 | 0.125 | 0.5 |
| 12061 | 0.06 | 0.5 |
| 12062 | 0.06 | 0.5 |
| 12063 | 0.06 | 0.5 |
| 12064 | 0.06 | 1 |

Table 2 illustrates that niclosamide has a lower MIC than vancomycin against the C difficile isolates tested.

TABLE 3

| Compounds | C. difficile Strain 7-6011209 MIC (µg/ml) | C. difficile Strain 12055 MIC (µg/ml) |
|---|---|---|
| Clioxanide | 0.031 | <0.08 |
| Closantel | 0.125 | 0.125 |
| Oxyclozanide | 0.25 | 0.25 |
| Rafoxanide | <0.08 | <0.08 |
| Tribromsalan | 0.125 | 0.25 |
| Vancomycin | 0.125 | 0.25 |

Example 2

Table 4 compares the properties of niclosamide with those of vancomycin, metronidazole, fidaxomicin. The data shown in Table 4 was obtained from published data together with data from the examples herein.

TABLE 4

| | Vancomycin | Metronidazole | Fidaxomicin | Niclosamide |
|---|---|---|---|---|
| Class | Glycopeptide | Nitroimidazole | Macrolide | Halogenated salicylanilide |

TABLE 4-continued

| | Vancomycin | Metronidazole | Fidaxomicin | Niclosamide |
|---|---|---|---|---|
| Dosing | TID, oral | TID, oral or IV | BID, oral | 1-4 times daily, oral |
| MIC90 (µg/mL) | 2[a] | 1[a] | 0.5[a] | 0.06-0.25[b] |
| Highest MIC observed (µg/mL) | 16[a] | >32[a] | 1 | 0.5 |
| Spectrum of activity | Gram+ | Gram +/− | Gram+ | Gram+ |
| Side effects[c] | Bladder pain, bloating, bloody urine, painful urination, fever, dry mouth, irregular heartbeat, loss of appetite, mood changes, muscle pain or cramps, numbness, rapid weight gain, shortness of breath, tiredness | Abdominal or stomach cramps, dizziness, heartburn, Spinning sensation. Trouble sleeping, congestion, dry mouth | Nausea, vomiting, abdominal pain, gastrointestinal hemorrhage, anemia, neutropenia | Nausea, retching, abdominal pain |

Footnotes:
[a]ANTIMICROBIAL AGENTS AND CHEMOTHERAPY, June 2002, p. 1647-1650' & 'CID 2012: 55 (Suppl 2) · S143'
[b]Data from Tables 3 and 4 herein.
[c]Data from product labels.

Example 3: Additional MIC Determinations

The MIC of the halogenated salicylanilides clioxanide, closantel, oxyclozanide, rafoxanide and tribromsalan was determined against 24 clinical isolate strains of *C. difficile*. Fidaxomicin, metronidazole and vancomycin were used as comparator compounds in the study. The comparator compounds represent the antibiotics most often used in current treatments of *C. difficile* infections.

Stock solutions of the test compounds and comparators were made in DMSO at a concentration of 1 mg/mL.

Microorganisms

The *C. difficile* strains used are shown in Table 5:

TABLE 5

| Name | MLST | Name | MLST |
|---|---|---|---|
| 7-6011209 | ST002 | 7-7363761 | ST008 |
| 7-7150288 | ST003 | 7-7200552 | ST017 |
| 7-7154992 | ST139 | 7-7150318 | ST059 |
| 7-6778909 | ST016 | 7-7150628 | ST034 |
| 7-6870430 | ST001 | 7-7149204 | ST006 |
| 7-7104022 | ST103 | 7-7116411 | ST005 |
| 7-5085357 | ST028 | 7-7150997 | ST049 |
| 7-7124449 | ST009 | 7-6854508 | ST013 |
| 12055 | — | 12063 | — |
| 12060 | — | 12064 | — |
| 12061 | — | 12065 | — |
| 12062 | — | 12066 | — |

Culture Medium

*C. difficile* strains were grown on *Brucella* blood agar+hemin+vitamin K [1], plates were incubated 44 to 48 hours at 36° C. under anaerobic conditions. Broth cultures were performed in *Brucella* bouillon supplemented with Isovitalex [2] according the instructions from the supplier (BBL). All cultures were performed under anaerobic conditions in an anaerobic chamber [3].

Antibacterial Activity

The antibacterial activity of the study compounds was determined using the following protocol.

1. Day 1: bacterial strain is isolated and incubated at 37° C. on *Brucella* blood agar+hemin+vitamin K.

2. Day 2: Inoculate 5 ml of *Brucella* bouillon supplemented with Isovitalex (BBI) with one isolated colony in 15 ml Falcon tube and incubated overnight at 36° C. in anaerobic conditions.

3. Day 3:

Dilute the antibiotics in BBI to their highest concentration (8 pg/ml in 2 ml).

Make a series of two fold dilutions in deep well 96 well plates.

Transfer 150 µl of the antibiotics solution to 96-well plates.

After 5-6 hours, the culture was stopped and $OD_{600}$ was measured. The culture is diluted to $10^6$ CFU/ml About 1 µl of this diluted culture is added in all wells in order to have $10^3$ cells per well.

Plates are incubated at 44 to 48 hours at 36° C. under anaerobic conditions.

4. Day 5: $OD_{600}$ is measured after incubation.

Inhibition calculated as follows:

$$\text{Inhibition} = 1 - \frac{OD \text{ antibiotic} - OD \text{ negative control}}{OD \text{ posititve control} - OD \text{ negative control}}$$

Results

The MIC values of the tested compounds against the 24 strains of *C. difficile* are shown in Table 6.

TABLE 6

| Strain | Clioxanide | Closantel | Oxyclozanide | Rafoxanide | Tribromsalan | Fidaxomycin | Metronidazole | Vancomycin |
|---|---|---|---|---|---|---|---|---|
| 7-6011209 | <0.008 | 0.016 | <0.008 | <0.008 | <0.008 | <0.008 | 0.031 | 0.031 |
| 7-7150288 | <0.008 | 0.031 | <0.008 | <0.008 | <0.008 | <0.008 | 0.063 | 0.5 |
| 7-7154992 | <0.008 | 0.063 | <0.008 | 0.016 | 0.063 | <0.008 | 1 | 0.5 |
| 7-6778909 | <0.008 | 0.031 | <0.008 | <0.008 | <0.008 | <0.008 | 0.25 | 05 |
| 7-6870430 | <0.008 | 0.031 | <0.008 | <0.008 | 0.016 | 0.016 | 1 | 0.5 |
| 7-7104022 | <0.008 | 0.25 | <0.008 | <0.008 | 1 | <0.008 | >8 | 2 |
| 7-5085357 | <0.008 | 0.016 | 0.016 | 0.016 | 0.016 | <0.008 | 1 | 0.5 |
| 7-7150997 | <0.008 | 0.016 | <0.008 | <0.008 | 0.16 | <0.008 | 0.031 | <0.008 |
| 7-7124449 | <0.008 | 0.25 | 0.031 | 0.031 | 0.063 | <0.008 | 2 | 0.5 |
| 7-6854508 | <0.008 | 0.25 | <0.008 | <0.008 | 0.031 | <0.008 | 1 | 0.5 |
| 7-7363761 | <0.008 | | | | | <0.008 | | |
| 7-7200552 | <0.008 | 0.5 | 0.25 | 0.063 | 0.25 | <0.008 | 2 | 1 |
| 7-7150318 | <0.008 | 0.63 | 0.016 | <0.008 | <0.008 | <0.008 | 1 | 1 |
| 7-7150628 | <0.008 | 0.063 | 0.31 | 0.31 | 0.031 | <0.008 | 0.5 | 1 |
| 7-7149204 | <0.008 | 0.31 | <0.008 | <0.008 | <0.008 | <0.008 | 0.5 | 0.5 |
| 7-7116411 | 0.125 | 0.25 | 0.125 | 0.031 | <0.008 | 2 | >16 | 2 |
| 12055 | <0.008 | 0.063 | 0.016 | <0.008 | 0.016 | <0.008 | 1 | 1 |
| 12060 | <0.008 | 0.125 | 0.031 | 0.031 | 0.063 | <0.008 | 1 | 0.5 |
| 12061 | <0.008 | 0.063 | 0.016 | 0.016 | 0.016 | <0.008 | 1 | 0.25 |
| 12062 | <0.008 | 0.063 | <0.008 | 0.016 | <0.008 | <0.008 | 0.125 | 0.125 |
| 12063 | <0.008 | 0.031 | 0.016 | <0.008 | 0.016 | <0.008 | 0.25 | 0.25 |
| 12064 | <0.008 | 0.031 | <0.008 | <0.008 | <0.008 | <0.008 | 0.031 | 0.5 |
| 12065 | <0.008 | 0.063 | 0.031 | 0.016 | 0.016 | <0.008 | 1 | 0.5 |
| 12066 | 0.063 | 0.5 | 0.125 | 0.063 | 0.031 | <0.008 | 1 | 0.5 |

Table 6 shows that the tested halogenated salicylanilides were active against the tested strains. The most active compounds were clioxanide, rafoxanide and oxyclozanide, which compared favourably with the activity of the comparator compound fidaxomycin. All of the tested halogenated salicylanilides generally exhibited lower MIC values than the comparator compounds, metronidazole and vancomycin.

REFERENCES

[1] H.-P. Schau, "J. F. MacFaddin, Media for Isolation-Cultivation-Identification-Maintenance of Medical Bacteria, Volume I. XI+929 S., 163 Abb., 94 Tab. Baltimore, London 1985. Williams and Wilkins. $90.00. ISBN: 0-683-05316-7," J. Basic Microbiol., vol. 26, no. 4, pp. 240-240, 1986.
[2] L. Pospisil, "[Isovitalex—a chemically definable enricher of culture media for *Neisseria gonorrhoeae*]," Ceskoslovenská Dermatol., vol. 46, no. 1, pp. 23-25, February 1971.
[3] A. N. Edwards, J. M. Suarez, and S. M. McBride, "Culturing and Maintaining *Clostridium difficile* in an Anaerobic Environment," J. Vis. Exp. JoVE, no. 79, p. e50787, September 2013.

Example 5: Sporulation Study

*Clostridium difficile* is a spore forming bacteria that causes severe diarrhea in healthcare settings. The spore is the infective agent, and is implicated in disease transmission and recurrence. Prevention or inhibition of spore formation may therefore minimise the risk of transmission and recurrence of infection, particularly in a hospital environment. Currently the main treatments used for the treatment of *C. difficile* infections are vancomycin, metronidazole, rifaximin and fidaxomicin. It has been shown that fidaxomicin inhibits *C. difficile* sporulation [1].

The halogenated salicylanilide, rafoxanide was tested assess its ability to inhibit spore formation. Fidaxomycin was used as a comparator in the study.

Methods
Bacterial Strain

The *C. difficile* strain used in the study was 7-6011209, a clinical isolate from the MLST group ST002.

Antimicrobial Agents

Rafoxanide and fidaxomicin (ex. Sigma-Aldrich) were prepared as 10 mg/mL stock solutions in dimethyl sulfoxide (DMSO). The compounds were diluted further to appropriate concentration in growth media prior to testing for their effect on sporulation.

Culture Media and Culture Conditions

*C. difficile* strains were grown and cultured in Brucella bouillon supplemented with Isovitalex as described above in Example 3.

Sporulation was carried out using Clospore medium [2], comprising Special Peptone Mix (Oxoid) 10 g/L, yeast extract 10 g/L, $(NH_4)_2 SO_4$ 0.6 g/L, $MgSO_4 \cdot 7H_2O$ 0.12 g/L, $CaCl_2) \cdot 2H_2O$ 0.08 g/L, $K_2CO_3$ 3.48 g/L, $KH_2PO_4$ 2.6 g/L, pH 7.9±0.1.

The germination medium was BHIS medium [3] containing 1 g/L of sodium taurocholate. BHIS medium comprises: Brain Heart Infusion 37 g/L, yeast extract 5 g/L, agar 15 g/L, L-cysteine 0.1% (w/v), glucose 0.5% (w/v) and $FeSO_4$ 0.09% (w/v).

All cultures were performed at 37° C. under anaerobic conditions in an anaerobic chamber as described in Example 3.

Sporulation Kinetics

*C. difficile* was grown overnight on blood agar plates. One colony was transferred to 10 mL of *Brucella* bouillon enriched with Isovitalex and grown overnight. Clospore medium containing the appropriate concentration of the test compound was inoculated at 1% with the overnight culture. Samples were withdrawn every 24 hours for quantitation of heat-resistant spores (survivors after incubation at 65° C. for 20 minutes). Spores were serially diluted in 0.09% NaCl and plated on BHIS agar supplemented with 0.1% sodium taurocholate to grow the spores for quantitation.

Concentrations of the test compounds were normalized to the MIC such that they were at least 8-fold above the MIC of the respective compound (8-fold for rafoxanide, and >8-fold for fidaxomicin).

Results

The impact of the test compounds on sporulation kinetics is shown in FIG. 1.

The negative control sporulates rapidly reached a value of $2 \times 10^5$ by 24 hours and approached its maximum count of approximately 10' by 48 hours sporulation. Rafoxanide, at 8-fold MIC, suppressed formation of spores throughout the 96 hour study period. The comparator compound fidaxomycin, at >8-fold MIC, suppressed formation of spores for the first 48 hours of the study, however, increased spore formation compared to rafoxanide occurred at the 72 and 96 hour time points.

The data illustrated by FIG. 1 shows that rafoxanide suppresses spore formation more effectively than fidaxomycin at a fixed effect level relative to MIC in this study. These results suggest that rafoxanide may inhibit the shedding of *C. difficile* spores and as such be effective in controlling the spread of infection in, for example, a hospital environment. The compound may also be useful in minimising the risk of recurrent infections in patients.

REFERENCES

[1] F. Babakhani, L. Bouillaut, P. Sears, C. Sims, A. Gomez, and A. L. Sonenshein, "Fidaxomicin inhibits toxin production in *Clostridium difficile*," *J. Antimicrob. Chemother.*, vol. 68, no. 3, pp. 515-522, March 2013.

[2] J. Perez, V. S. Springthorpe, and S. A. Sattar, "Clospore: a liquid medium for producing high titers of semi-purified spores of *Clostridium difficile*," *J. AOAC Int.*, vol. 94, no. 2, pp. 618-626, April 2011.

[3] C. J. Smith, S. M. Markowitz, and F. L. Macrina, "Transferable tetracycline resistance in *Clostridium difficile*," *Antimicrob. Agents Chemother.*, vol. 19, no. 6, pp. 997-1003, June 1981.

The invention is further illustrated by the following numbered clauses:

1. A halogenated salicylanilide, or a pharmaceutically acceptable salt or ester thereof for use in the treatment of an infection in a subject caused by *Clostridium* bacteria.
2. The halogenated salicylanilide for the use of Clause 1 wherein the infection is caused by *Clostridium difficile*.
3. The halogenated salicylanilide for the use of Clause 2, wherein the infection is a *Clostridium difficile* associated disease.
4. The halogenated salicylanilide for the use of Clause 3, wherein *Clostridium difficile* associated disease is diarrhoea, colitis (for example pseudomembranous colitis) or toxic megacolon.
5. The halogenated salicylanilide for the use of any of Clauses 1 to 4, wherein the *Clostridium* infection is an antibiotic induced *Clostridium* infection, wherein the antibiotic is other than a halogenated salicylanilide.
6. The halogenated salicylanilide for the use of Clause 5, wherein the antibiotic other than a halogenated salicylanilide is selected from clindamycin, a cephalosporin (for example cefotaxime and ceftaidime), ampicillin, amoxicillin and a quinolone (for example a fluoroquinolone, optionally ciprofloxaxin or levofloxacin).
7. The halogenated salicylanilide for the use of any of Clauses 1 to 6, wherein the *Clostridium* infection has not been treated with an antibiotic prior to administration of the halogenated salicylanilide to the subject.
8. The halogenated salicylanilide for the use of any of Clauses 1 to 6, wherein the subject has a *Clostridium* infection which has recurred following treatment with an antibiotic other than a halogenated salicylanilide.
9. The halogenated salicylanilide for the use of Clause 8, wherein *Clostridium* infection has recurred after being treated with an antibiotic selected from metronidazole, vancomycin and fidaxomicin.
10. The halogenated salicylanilide for the use of any of Clauses 1 to 6, wherein the *Clostridium* infection is refractory to a prior antibiotic treatment other than a halogenated salicylanilide.
11. The halogenated salicylanilide for the use of Clause 10, wherein the prior antibiotic treatment is selected from metronidazole, vancomycin and fidaxomycin.
12. The halogenated salicylanilide for the use of any preceding Clause wherein the infection is caused by the NAP1/027/BI *C. difficile* strain.
13. The halogenated salicylanilide for the use of any preceding Clause, wherein the halogenated salicylanilide is of the formula (I):

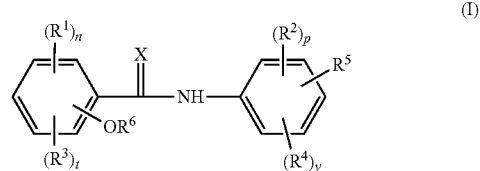

wherein
X is O or S;
$R^1$ and $R^2$ are at each occurrence independently selected from halo;
$R^3$ and $R^4$ are at each occurrence independently selected from H, $C_{1-6}$ alkyl, $-OR^{41}$, $-NO_2$ and $-CN$;
$R^5$ is H or $-L^1-R^7$;
$R^6$ is H or $-C(O)R^{42}$;
$L^1$ is selected from a bond, O, S, or $-(CR^{43}R^B)_o-$, wherein o is 1 or 2;
$R^6$ is phenyl, unsubstituted or substituted with 1, 2, or 3 groups selected from halo, $C_{1-4}$ alkyl, $-OR^{41}$, $-NO_2$ and $-CN$;
$R^{41}$, $R^{42}$, $R^{43}$ and $R^{44}$ are at each occurrence independently selected from H and $C_{1-4}$ alkyl;
$R^B$ is at each occurrence selected from H, $C_{1-4}$ alkyl and $-CN$;
n and p are each independently selected from 0, 1, 2, 3 or 4, with the proviso that n+p is at least 1;
t and v are independently selected from 0, 1 and 2;
or a pharmaceutically acceptable salt, or ester thereof
14. The halogenated salicylanilide for the use of Clause 13, wherein X is O.
15. The halogenated salicylanilide for the use of Clause 13 or Clause 14, wherein $R^6$ is H.
16. The halogenated salicylanilide for the use of any of Clauses 13 to 15, wherein $R^3$ and $R^4$ are at each occurrence independently selected from H, $C_{1-4}$ alkyl, $-OR^{41}$ and $-NO_2$.
17. The halogenated salicylanilide for the use of any of Clauses 13 to 16, wherein $L^1$ is selected from O, $-CH_2-$ and $-CH(CN)-$.
18. The halogenated salicylanilide for the use of any of Clauses 13 to 17, wherein $R^7$ is phenyl unsubstituted or substituted with 1, 2 or 3 groups selected from halo.
19. The halogenated salicylanilide for the use of any of Clauses 1 to 12, wherein the halogenated salicylanilide is selected from

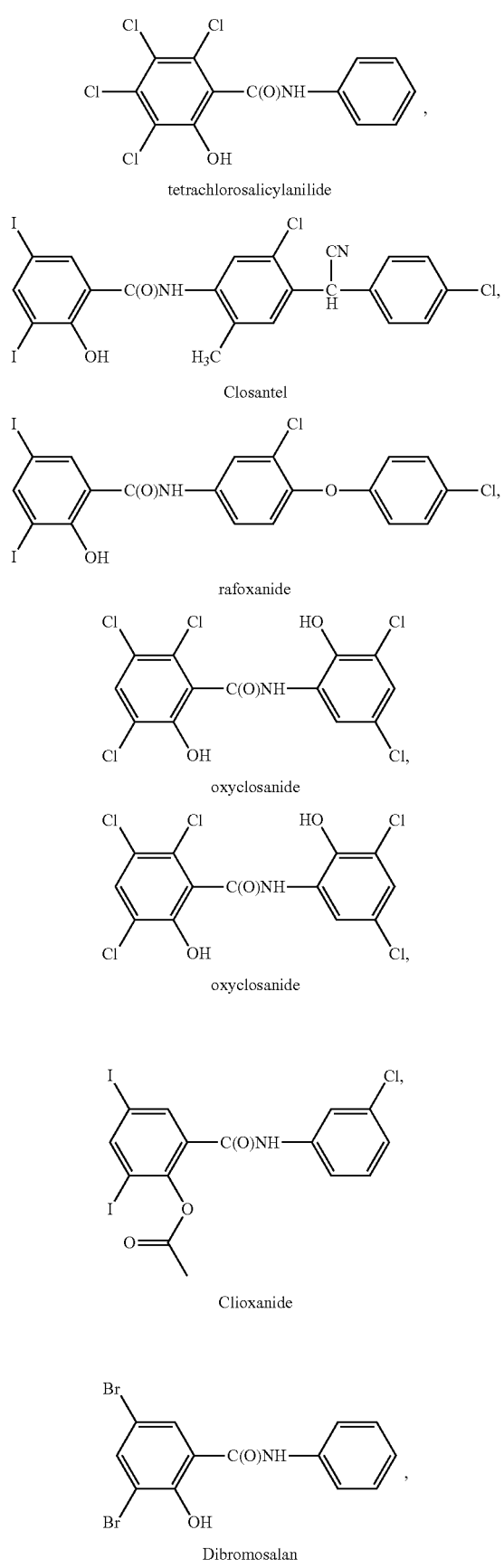

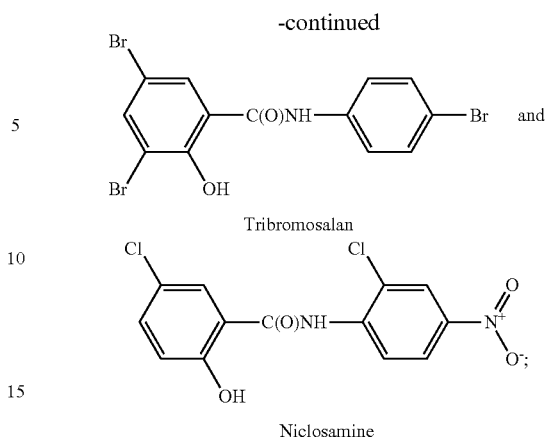

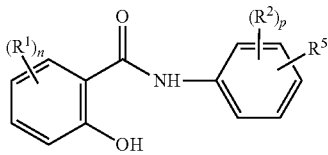

or a pharmaceutically acceptable salt or ester thereof.

20. The halogenated salicylanilide for the use of any of Clauses 1 to 12, wherein the halogenated salicylanilide is selected from the group consisting of niclosamide, clioxanide, closantel, oxyclozanide, rafoxanide, tribromosalan, or a pharmaceutically acceptable salt or ester thereof.

21. Use of a halogenated salicylanilide, or a pharmaceutically acceptable salt or ester thereof for the manufacture of a medicament for the treatment of an infection in a subject caused by *Clostridium* bacteria.

22. A method of treating an infection caused by *Clostridium* bacteria in a subject, the method comprising administering to said subject an effective amount of a halogenated salicylanilide, or a pharmaceutically acceptable salt or ester thereof.

23. The halogenated salicylanilide for the use of any of Clauses 1 to 20, the use of Clause 21 or the method of Clause 22, wherein the halogenated salicylanilide is orally administered to the subject.

24. The halogenated salicylanilide for the use of any of Clauses 1 to 20, the use of Clause 21 or the method of Clause 22, wherein the subject is a human or warm blooded animal, optionally wherein the subject is a human.

25. The halogenated salicylanilide for the use of any of Clauses 1 to 20, the use of Clause 21 or the method of Clause 22, wherein the subject is a human aged 65 years or older

The invention claimed is:
1. A method of treating an infection caused by *Clostridium difficile* bacteria in a subject, the method comprising administering to said subject an effective amount of a halogenated salicylanilide, or a pharmaceutically acceptable salt or ester thereof, wherein the halogenated salicylanilide is of the formula:

wherein
$R^1$ and $R^2$ are each independently halo;
$R^5$ is H or $-L^1-R^7$;
$L^1$ is selected from the group consisting of a bond and O;

R⁷ is phenyl, unsubstituted or substituted with 1 or 2 groups each independently selected from the group consisting of halo and $C_{1-4}$ alkyl;

n is 1 or 2;

p is 0 or 1.

2. The method of claim 1, wherein n is 2 and $R^1$ is I.

3. The method of claim 1, wherein $R^2$ is independently selected from I and Cl.

4. The method of claim 1, wherein p is 1 and $R^2$ is I or Cl.

5. The method of claim 1, wherein $R^5$ is H.

6. The method of claim 1, wherein $R^5$ is H, p is 1 and $R^2$ is I or Cl.

7. The method of claim 1, wherein:

$R^5$ is H;

p is 1;

$R^2$ is I or Cl;

n is 2; and $R^1$ is I.

8. The method of claim 1, wherein $R^5$ is $-L^1-R^7$, and $R^7$ is unsubstituted phenyl.

9. The method of claim 1, wherein $R^5$ is $-L^1-R^7$, $L^1$ is O and $R^7$ is phenyl substituted with one $CH_3$.

10. The method of claim 1, wherein the *Clostridium difficile* infection is associated with a disease selected from the group consisting of diarrhoea, colitis, pseudomembranous colitis and toxic megacolon.

11. The method of claim 1, wherein the *Clostridium difficile* infection is an antibiotic induced *Clostridium difficile* infection, wherein the antibiotic which induced the infection is other than the halogenated salicylanilide.

12. The method of claim 11, wherein the antibiotic which induced the infection is selected from clindamycin, a cephalosporin, cefotaxime, ceftazidime, ampicillin, amoxicillin, a quinolone, a fluoroquinolone, ciprofloxaxin and levofloxacin.

13. The method of claim 1, wherein the *Clostridium difficile* infection is induced by a gastric acid suppressive agent.

14. The method of claim 1, wherein the *Clostridium difficile* is resistant to an antibiotic agent other than the halogenated salicylanilide.

15. The method of claim 1, wherein the *Clostridium difficile* is a *Clostridium difficile* strain that is resistant to an antibiotic agent selected from metronidazole, vancomycin, fidaxomicin and a rifamycin.

16. The method of claim 1, wherein the *Clostridium difficile* infection has not been treated with an antibiotic prior to administration of the halogenated salicylanilide to the subject.

17. The method of claim 1, wherein the subject has a recurrent *Clostridium difficile* infection.

18. The method of claim 17, wherein the recurrent *Clostridium difficile* infection has recurred following prior treatment with an antibiotic other than the halogenated salicylanilide.

19. The method of claim 17, wherein the *Clostridium difficile* infection has recurred after being treated with an antibiotic selected from metronidazole, vancomycin, fidaxomicin and a rifamycin.

20. The method of claim 1, wherein treatment of the subject with the halogenated salicylanilide, or a pharmaceutically acceptable salt or ester thereof, prevents or inhibits sporulation of *C. difficile* in the subject.

21. The method of claim 1, wherein the halogenated salicylanilide, or a pharmaceutically acceptable salt or ester thereof, is orally administered to the subject.

22. The method of claim 1, wherein the subject is a human.

* * * * *